ns et al.

(12) United States Patent  (10) Patent No.: US 10,525,160 B2
Bezwada et al.  (45) Date of Patent: *Jan. 7, 2020

(54) MULTI-PUTTY ADHESIVE AND CEMENT COMPOSITIONS FOR TISSUE HEMOSTASIS, REPAIR AND RECONSTRUCTION

(71) Applicant: Abyrx, Inc., Irvington, NY (US)

(72) Inventors: Rao Bezwada, Irvington, NY (US); Aniq Darr, Irvington, NY (US); Richard L. Kronenthal, Irvington, NY (US); John Pacifico, Irvington, NY (US)

(73) Assignee: Abyrx, Inc., Irvington, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/037,572

(22) Filed: Jul. 17, 2018

(65) Prior Publication Data

US 2019/0099514 A1 Apr. 4, 2019

Related U.S. Application Data

(63) Continuation of application No. 15/073,906, filed on Mar. 18, 2016, now Pat. No. 10,046,083, which is a continuation of application No. 14/241,142, filed as application No. PCT/US2012/053778 on Sep. 5, 2012, now Pat. No. 9,314,547.

(60) Provisional application No. 61/656,720, filed on Jun. 7, 2012, provisional application No. 61/553,294, filed on Oct. 31, 2011, provisional application No. 61/533,069, filed on Sep. 9, 2011.

(51) Int. Cl.
*A61L 24/04* (2006.01)
*A61L 27/18* (2006.01)
*A61L 27/44* (2006.01)
*A61L 27/58* (2006.01)
*A61L 24/00* (2006.01)

(52) U.S. Cl.
CPC ......... *A61L 24/046* (2013.01); *A61L 24/0036* (2013.01); *A61L 24/0042* (2013.01); *A61L 24/0073* (2013.01); *A61L 27/18* (2013.01); *A61L 27/44* (2013.01); *A61L 27/58* (2013.01); *A61L 2400/04* (2013.01); *A61L 2430/02* (2013.01)

(58) Field of Classification Search
None
See application file for complete search history.

(56) References Cited

U.S. PATENT DOCUMENTS

| | | |
|---|---|---|
| 3,995,641 A | 12/1976 | Kronenthal et al. |
| 4,724,250 A | 2/1988 | Schubert et al. |
| 4,829,099 A | 5/1989 | Fuller et al. |
| 5,159,044 A | 10/1992 | Bogner |
| 5,810,956 A | 9/1998 | Tanis et al. |
| 6,140,452 A | 10/2000 | Felt et al. |
| 6,306,177 B1 | 10/2001 | Felt et al. |
| 6,533,821 B1 | 3/2003 | Lally |
| 7,270,813 B2 | 9/2007 | Shimp et al. |
| 7,291,345 B2 | 11/2007 | Winterbottom et al. |
| 7,772,352 B2 | 8/2010 | Bezwada |
| 7,955,616 B2 | 6/2011 | Kronenthal |
| 7,964,207 B2 | 6/2011 | Deslauriers et al. |
| 7,985,414 B2 | 7/2011 | Knaack et al. |
| 8,002,843 B2 | 8/2011 | Knaack et al. |
| 8,282,953 B2 | 10/2012 | Drapeau et al. |
| 8,425,893 B2 | 4/2013 | Knaack et al. |
| 8,431,147 B2 | 4/2013 | Drapeau et al. |
| 8,475,824 B2 | 7/2013 | McKay |
| 8,506,983 B2 | 8/2013 | Mohan et al. |
| 8,562,293 B2 | 10/2013 | Englander |
| 8,628,761 B2 * | 1/2014 | Adhikari ................. A61L 27/18 424/78.08 |
| 8,771,719 B2 | 7/2014 | Shimp et al. |
| 9,107,751 B2 | 8/2015 | Winterbottom et al. |
| 9,314,547 B2 | 4/2016 | Bezwada et al. |
| 9,333,276 B2 * | 5/2016 | Guelcher ................ A61L 27/44 |
| 10,046,083 B2 | 8/2018 | Bezwada et al. |
| 2005/0013793 A1 | 1/2005 | Beckman et al. |
| 2007/0191963 A1 | 8/2007 | Winterbottom et al. |
| 2009/0081270 A9 | 3/2009 | Moore et al. |
| 2009/0292029 A1 | 11/2009 | Bezwada |
| 2009/0304773 A1 | 12/2009 | Milbocker et al. |
| 2010/0068171 A1 | 3/2010 | Guelcher et al. |
| 2010/0112032 A1 | 5/2010 | Guelcher et al. |
| 2010/0197855 A1 | 8/2010 | Blom |
| 2010/0210748 A1 | 8/2010 | Leimenstoll et al. |
| 2010/0260702 A1 | 10/2010 | Bezwada |
| 2010/0297082 A1 | 11/2010 | Guelcher et al. |
| 2011/0236501 A1 | 9/2011 | Guelcher et al. |
| 2011/0237704 A1 | 9/2011 | Guelcher et al. |
| 2012/0035610 A1 | 2/2012 | Deslauriers et al. |
| 2012/0269892 A1 | 10/2012 | Mossaad et al. |
| 2013/0236513 A1 | 9/2013 | Guelcher et al. |

FOREIGN PATENT DOCUMENTS

| | | |
|---|---|---|
| WO | WO-2004/009227 A2 | 1/2004 |
| WO | WO-2010/011941 A2 | 1/2010 |

OTHER PUBLICATIONS

International Search Report for PCT/US2012/053778 dated Mar. 4, 2013.

(Continued)

*Primary Examiner* — Tae H Yoon

(74) *Attorney, Agent, or Firm* — Cooley LLP; Ivor R. Elrifi; Matthew Pavao

(57) ABSTRACT

The disclosure relates to polyurethane and polyureaurethane based putty compositions which harden into a fully cured solid form at room temperature and body temperature and are suitable for use as a bone cement, bone substitute, hard tissue adhesive, or bone hemostatic agent.

18 Claims, No Drawings

(56) References Cited

OTHER PUBLICATIONS

Supplementary European Search Report for Application No. 12830247.8, 6 pages, dated Apr. 28, 2015.

* cited by examiner

MULTI-PUTTY ADHESIVE AND CEMENT COMPOSITIONS FOR TISSUE HEMOSTASIS, REPAIR AND RECONSTRUCTION

CROSS-REFERENCE TO RELATED APPLICATIONS

This application is a Continuation of U.S. patent application Ser. No. 15/073,906, filed Mar. 18, 2016, now U.S. Pat. No. 10,046,083, issued on Aug. 14, 2018, which is a Continuation of U.S. patent application Ser. No. 14/241,142, filed Feb. 26, 2014, now U.S. Pat. No. 9,314,547, issued on Apr. 19, 2016, which is a National Stage Application, filed under 35 U.S.C. 371, of International Application No. PCT/US2012/053778, filed Sep. 5, 2012, which claims the benefit of, and priority to, U.S. Patent Application No. 61/656,720, filed Jun. 7, 2012, U.S. Patent Application No. 61/553,294, filed Oct. 31, 2011 and U.S. Patent Application No. 61/553,069, filed Sep. 9, 2011. The contents of each of these applications are herein incorporated by reference in their entirety.

FIELD OF THE INVENTION

The present invention relates to the field of implantable polymeric compositions for medical use in a patient to aid in repair or reconstruction of tissue, such as bone. Specifically to the field of polyurethane-based cements, and putties for use in bone hemostasis, repair and reconstruction. The putty compositions may comprise a mixture of two or more individual putties (multi-putty) formed through mixing of one or more reactive components and one or more additive (filler) components. Also disclosed herein are methods of using the putty compositions in medical applications to repair gaps or fractures, or to aid in tissue growth or adhesion. In particular, the subject matter herein provides a putty composition that is formed from two or more individual putties that are obtained by mixing a liquid component and a filler component.

INCORPORATION BY REFERENCE

Each of the applications and patents cited in this text, as well as each document or reference cited in each of the applications and patents (including during the prosecution of each issued patent; "application cited documents"), and each of the U.S. and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference. Documents incorporated by reference into this text may be employed in the practice of the invention.

BACKGROUND OF THE INVENTION

Bone cements are used surgically to assist in the attachment of artificial implants to living bone and for bone repair and reconstruction. The most commonly used bone cements comprise polymers formed from a mixture of polymethylmethacrylate (PMMA) and a monomer, such as methylmethacrylate (MMA), reacting in the presence of a polymerization activator or reaction initiator. These conventional PMMA-based cements have several disadvantages. Typically, the excessive exotherm during the curing process of conventional cements may itself cause tissue damage. In addition, conventional cements are not easily degradable or absorbable in vivo. This may present both an increased risk of infection and/or an inflammatory reaction at the site and may inhibit the growth of new bone at the site.

Biodegradable polymers have become increasingly important for a variety of biomedical applications including biomedical implants, such as sutures, stents, and coatings applied to those implants, tissue engineering scaffolds, and soft-tissue adhesives. Segmented polyurethane elastomers in particular have come into wide use as biomaterials due to their superior mechanical properties and chemical versatility. PCT International Application Publication No. WO 2004009227 describes certain degradable polyurethane compositions for use as tissue engineering scaffolds. U.S. Pat. No. 6,306,177 by Felt, et al., describes certain degradable polyurethanes for in situ tissue repair. U.S. Patent Application Publication No. 20050013793 by Beckman, et al., also describes degradable polyurethanes for e.g., tissue engineering and particularly for bone repair and replacement. U.S. Pat. No. 4,829,099 by Fuller, et al., describes certain absorbable polyisocyanates for use as surgical adhesives. U.S. Pat. Nos. 8,002,843 and 7,985,414 by Knaack, et al., describe a biodegradable polyisocyante (such as lysine diisocyanate) with an optionally hydroxylated biomolecule to form a degradable polyurethane. U.S. Pat. No. 7,964,207 by Deslaurier, et al., describes porous, non-absorbable, osteoconductive polyurethane compositions having mechanical properties consistent for use in bone repair.

For the preparation of implantable polyurethanes, it is conventional to mix, in the operating room, pre-weighed amounts of a diisocyanate, a polyol, a chain extender and, optionally, a filler that is often ceramic-like, polymeric or a cellulosic material. Optionally, an antimicrobial agent, e.g., tobramycin, may be added to reduce the incidence of postoperative infection. The components are usually liquid at ambient temperature and require mixing liquids and, sometimes, liquids with solids in a suitable container using a suitable stirring mechanism.

Liquid component settable polymers (e.g., Kryptonite) in medical use traditionally require mixing and application of the activated polymer as a liquid. Polymers provided in this way are difficult to apply, may become slippery upon exposure to body fluids, stick to surgical gloves, instruments and fixation devices such as wires, plates and screws. In some instances, polymer misapplication may result in damage to medical devices, such as drains and catheters, during their removal.

Despite progress in the development of polyurethane-based biomedical materials, there remains a need for non-toxic, readily biodegradable or absorbable compositions having suitable mechanical properties for bone repair and reconstruction. The present invention provides polyurethane-based compositions suitable for use in bone repair and reconstruction, specifically as bone cements, bone substitutes or hemostatic agents.

SUMMARY OF THE INVENTION

The present invention provides curable, absorbable polyurethane and polyureaurethane compositions comprising a polyaromatic polyisocyanate and one or more polyols and/or polyamines. Preferably, the composition is provided in binary form, more specifically in the form of two putties which, when mixed or kneaded together form a settable hemostatic agent, bone substitute or cement. As used herein the term "putty" refers to soft moldable, preferably non-elastic, cohesive compositions, most often formed as viscous suspensions or dispersions of particulates within a liquid. The inventive putties may also be formed from monolithic compositions of waxes and soft polymers: The putties of the invention are distinguished from the transitional "taffy" phases which occur during the setting process of polyurethanes and other settable compositions. Accordingly, in one embodiment, the present invention provides a binary package or article of manufacture comprising a first component and a second component, wherein the first component contains a curable polyaromatic di- or polyisocyanate having a hydrolysable linkage bridging at least two of the aromatic rings and the second component contains a polyol or polyamine, or mixtures thereof. In another embodiment, the invention provides a binary package or article of manufacture comprising a first component and a second component, wherein the first component contains a curable prepolymer of a polyaromatic polyisocyanate having a hydrolysable linkage bridging at least two of the aromatic rings and a polyol in the form of a putty and the second component, also in the form of a putty, containing an isocyanate, an absorbable polyol, a chain extender and none, or one or more additives. In another embodiment, the invention provides a curable, absorbable polymeric composition formed by the reaction of two or more individual putty compositions, wherein a first putty composition comprises one or more reactive components and one or more additive components and a second putty composition comprises one or more reactive components and one or more additive components. Preferably, the one or more reactive components in the first putty composition comprise an isocyanate and/or mixtures of isocyanates, and most preferably the isocyanate is [5-[2-[2-(4-isocyanatobenzoyl)oxypropanoyloxy]-ethoxy]-1-methyl-2-oxo-pentyl]-4-isocyanatobenzoate (ALD). Also preferred is an embodiment in which the second putty comprises one or more polyols, hydroxyl terminated polymers of glycolide, lactide, p-dioxanone, trimethylene carbonate and/or caprolactone, polyethylene glycol, a copolymer of ethylene oxide and propylene oxide (poloxamers), 1,2-ethanediol (ethylene glycol), 1,2-propanediol (propylene glycol), 1,3-propanediol, 1,4-butanediol, 1,5-pentanediol, 1,3-cyclopentanediol, 1,6-hexanediol, 1,4-cyclohexanediol, 1,8-octanediol, glycerol, polyethylene glycol and polypropylene glycol with molecular weights of 400-10000, and combinations thereof. In accordance with the above embodiments, the one or more additive components in each individual reactive putty composition may comprise a carbonate or bicarbonate selected from calcium carbonate, magnesium carbonate, aluminum carbonate, iron carbonate, zinc carbonate, calcium bicarbonate, sodium bicarbonate, embedded particles of bone, demineralized bone, bone morphogenetic protein, hydroxyapatite, calcium phosphate, siliconized calcium phosphate, absorbable phosphate glass, an inorganic material, a bone substitute material, a carbonate selected from magnesium carbonate, aluminum carbonate, iron carbonate, zinc carbonate, calcium carbonate, sodium carbonate, and a bicarbonate of magnesium, aluminum, iron, or zinc, and combinations thereof. In one embodiment, the one or more reactive components in the second putty composition comprises a polyurethane formed from one or more polyols reacted with isocyanate. In accordance with any of these embodiments, the composition may further comprise one or more putties in addition to the two putties of the binary composition.

The polyurethane compositions of the invention are formed from the reaction of a polyaromatic polyisocyanate, one or more polyols and/or polyamines and, optionally, a polyol and/or a polyamine as a chain extender. Thus, as used throughout the present disclosure with reference to the compositions of the invention, the term "comprising" refers to the polyurethane or polyureaurethane reaction product of an isocyanate, a polyol/polyamine and, optionally, a polyol and/or a polyamine as a chain extender.

The polyurethane compositions of the invention are low exotherm, biocompatible compositions suitable for use in vivo, particularly as a bone cement or hemostatic agent during bone repair and reconstructive surgery. For example, the curable, moldable polyurethane compositions of the invention are well-suited for use in the repair of cranial defects and cranioplasty applications as well as for repair and reconstruction of the sternum. The term nontoxic as used herein refers to the biocompatibility of the polyurethane compositions of the invention. The compositions of the invention are absorbable, in part due to a hydrolysable linkage bridging the aromatic rings. In certain embodiments, the hydrolysable linkage is derived from glycolic acid, lactic acid, caprolactone, or p-dioxanone. Both the curable polyurethane compositions of the invention and their degradation products are biocompatible. Unlike certain prior art aromatic isocyanates, the present compositions do not degrade into toxic byproducts such as, for example, aromatic diamines.

In certain embodiments, curable, absorbable polyurethane and polyureaurethane compositions of the invention further comprise one or more hydrolysable polyols and/or polyamines. In one embodiment, the polyol is selected from hydroxyl terminated copolymers of glycolide, lactide, p-dioxanone, trimethylene carbonate and/or caprolactone, polyethylene glycol, a copolymer of ethyelene oxide and propylene oxide (Pluronic). In another embodiment, the polyol is selected from a polycaprolactone co-glycolide or a polycaprolactone co-lactide, or combinations thereof.

The polyurethane and polyureaurethane compositions of the invention may further comprise one or more chain extenders or crosslinkers. In one embodiment, the curable, absorbable polyurethane and polyureaurethane compositions of the invention are crosslinked. In another embodiment, the curable, absorbable polyurethane and polyureaurethane compositions of the invention are not crosslinked. In one embodiment, the one or more chain extenders or crosslinkers is selected from a natural or synthetic aliphatic polyol. In one embodiment, the composition is formed by a process that includes one or more chain extenders selected from 1,2-ethanediol (ethylene glycol), 1,2-propanediol (propylene glycol), 1,3-propanediol, 1,4-butanediol, 1,5-pentanediol, 1,3-cyclopentanediol, 1,6-hexanediol, 1,4-cyclohexanediol, 1,8-octanediol, glycerol, polyethylene glycol and polypropylene glycol with molecular weights of 500-10000, and combinations thereof.

In one embodiment, the curable, absorbable polyurethane compositions of the invention comprise a glycolide linked diisocyanate and a polycaprolactone-co-glycolide polyol. In one embodiment, the composition further comprises butanediol, e.g., as a chain extender. In one embodiment, the composition further comprises one or more of water, a carboxylic acid, e.g., benzoic acid, and a divalent or polyvalent metal salt.

In one embodiment, the curable, absorbable polyurethane compositions of the invention comprise a lactide linked diisocyanate and a polycaprolactone-co-glycolide polyol. In one embodiment, the composition further comprises butanediol, e.g., as a chain extender. In one embodiment, the composition further comprises one or more of water, a carboxylic acid, e.g., benzoic acid, and a divalent or polyvalent metal salt.

In one embodiment, the curable, absorbable polyurethane compositions of the invention comprise a tetraisocyanate. In one embodiment, the tetraisocyanate is a caprolactone ethylene glycol linked phenylalanine diisocyante. In one embodiment, the composition further comprises one or more of water, a carboxylic acid, e.g., benzoic acid, and a divalent or polyvalent metal salt.

In one embodiment, the curable, absorbable polyurethane and polyureaurethane compositions of the invention further comprise one or more particulate materials. In one embodiment, the one or more particulate materials is present in an amount that is up to about 80% of the composition by weight. In one embodiment, the one or more particulate materials is a carbonate or bicarbonate selected from calcium carbonate, magnesium carbonate, aluminum carbonate, iron carbonate, zinc carbonate, calcium bicarbonate, and sodium bicarbonate. In one embodiment, the one or more particulate materials do not comprise calcium carbonate or calcium phosphate. In one embodiment, the one or more particulate materials is selected from embedded particles of bone, demineralized bone, bone morphogenetic protein, hydroxyapatite, calcium phosphate, siliconized calcium phosphate, absorbable phosphate glass, an inorganic material, a bone substitute material, a carbonate selected from magnesium carbonate, aluminum carbonate, iron carbonate, zinc carbonate, calcium carbonate, sodium carbonate, and a bicarbonate of magnesium, aluminum, iron, or zinc, or a combination of any of the foregoing. In one embodiment, the compositions of the invention do not comprise a particulate material. Other possible additives are starch, carboxymethyl starch, carboxymethyl cellulose, oxidized cellulose, antimicrobial agents, colorants, X-ray opaque substances and water (if foaming is desired).

In general, the curable, absorbable polyurethane and polyureaurethane compositions of the invention are formed by the reaction of one or more polyaromatic di- or polyisocyanates with one or more diols or polyols and/or polyamines. The process for forming the polyurethane and polyureaurethane compositions of the invention may also include the addition of an optional chain extender or crosslinker. In one embodiment, the compositions of the invention are formed in the absence of a crosslinker. In one embodiment, the composition is formed by a process of combining a polyol and/or a polyamine, a polyaromatic di- or poly-isocyanate, and a carboxylic acid. In one embodiment, the carboxylic acid is selected from benzoic acid, malic acid, and succinnic acid. In another embodiment, the composition is formed by a process of combining a polyol and/or polyamine, a polyaromatic polyisocyanate, and water.

In another embodiment, the package or article of manufacture comprises a first component and a second component wherein the first component contains a curable polyaromatic di- or polyisocyanate having at least one hydrolysable linkage bridging at least two of the aromatic rings and is in the form of putty-like consistency while the second component contains a polyol and/or a polyamine, also in the form of putty-like consistency. In this embodiment, the putties of the first and of the second component are mixed or kneaded together at the time of use to form a settable hemostatic agent or bone void filler or bone cement. In component 1, a small amount of polyol may be added to form a putty-like prepolymer while a small amount of isocyanate may be added to component 2 to form a putty-like polyol derivative. Other additives such as chain extenders, catalysts, cross-linking agents and bulking agents such as calcium phosphate, etc., also may be added to component 2.

The invention also provides a package or article of manufacture containing the polyurethane or polyureaurethane composition of claim 1 in its fluid form, wherein the package or article is maintained at a temperature below 0 C. In another embodiment, the invention provides a binary package or article of manufacture comprising a first component and a second component, wherein the first component contains a curable polyaromatic di- or polyisocyanate having a hydrolysable linkage bridging at least two of the aromatic rings and the second component contains a polyol and/or a polyamine. In another embodiment, the binary package or article of manufacture comprises a first component and a second component, wherein the first component contains a curable prepolymer of a polyaromatic di- or polyisocyanate having a hydrolysable linkage bridging at least two of the aromatic rings and a polyol and/or polyamine and the second component contains a chain extender. In certain embodiments, the components of the package or article of manufacture are sterile or sterilizable.

The invention further provides methods for applying the compositions of the invention to a surface. In one embodiment, the method comprises a single step of applying a curable polyurethane or polyureaurethane composition of the invention to the surface, with or without a catalyst. In another embodiment, the method comprises mixing an isocyanate-terminated prepolymer of the compositions of the invention with the polyol/polyamine component just prior to application to the surface, with or without a catalyst. The prepolymer is formed from the reaction of excess isocyanate with the polyol/polyamine component.

In one aspect of the subject matter disclosed herein, a composition comprising a mixture of two or more individual putty compositions is provided, wherein a first putty composition comprises one or more reactive components and one or more additive (filler) components and a second putty composition comprises one or more reactive components and one or more additive (filler) components.

In some embodiments, the one or more reactive components in the first putty composition comprise an isocyanate and/or mixtures of isocyanates. In some embodiments, the isocyanate is [5-[2-[2-(4-isocyanatobenzoyl)oxypropanoyloxy]-ethoxy]-1-methyl-2-oxo-pentyl]-4-isocyanatobenzoate (ALD).

In some embodiments, the second putty comprises one or more polyols, hydroxyl terminated polymers of glycolide, lactide, p-dioxanone, trimethylene carbonate and/or caprolactone, polyethylene glycol, a copolymer of ethylene oxide and propylene oxide (poloxamers), 1,2-ethanediol (ethylene glycol), 1,2-propanediol (propylene glycol), 1,3-propanediol, 1,4-butanediol, 1,5-pentanediol, 1,3-cyclopentanediol, 1,6-hexanediol, 1,4-cyclohexanediol, 1,8-octanediol, glycerol, polyethylene glycol and polypropylene glycol with molecular weights of 400-10000, and combinations thereof.

The one or more additive components in each individual reactive putty composition may comprise a carbonate or bicarbonate selected from calcium carbonate, magnesium carbonate, aluminum carbonate, iron carbonate, zinc carbonate, calcium bicarbonate, sodium bicarbonate, embedded particles of bone, demineralized bone, hone morphogenetic protein, hydroxyapatite, calcium phosphate, silicated calcium phosphate, absorbable phosphate glass, an inorganic material, a bone substitute material, a carbonate selected from magnesium carbonate, aluminum carbonate, iron carbonate, zinc carbonate, calcium carbonate, sodium carbonate, and a bicarbonate of magnesium, aluminum, iron, or zinc, and combinations thereof.

In some embodiments, the one or more reactive components in the second putty composition comprises polyurethane formed from one or more polyols reacted with isocyanate, which may be [5-[2-[2-(4-isocyanatobenzoyl) oxypropanoyloxy]-ethoxy]-1-methyl-2-oxo-pentyl]-4-isocyanatobenzoate (ALD).

In some embodiments, the one or more polyols comprise hydroxyl terminated polymers of glycolide, lactide, p-dioxanone, trimethylene carbonate and/or caprolactone, polyethylene glycol, a copolymer of ethylene oxide and propylene oxide (poloxamers), 1,2-ethanediol (ethylene glycol), diethylene glycol, 1,2-propanediol (propylene glycol), 1,3-propanediol, 1,4-butanediol, 1,5-pentanediol, 1,3-cyclopentanediol, 1,6-hexanediol, 1,4-cyclohexanediol, 1,8-octanediol, glycerol, polyethylene glycol and polypropylene glycol with molecular weights of 400-10000, and combinations thereof.

In certain embodiments, the compositions disclosed herein may further comprise a third, a fourth, a fifth (or more) putty compositions, and/or additional putty additives.

In other aspects, a sterilized composition comprising a mixture of two or more individual putty compositions is provided, as further described herein.

In some embodiments, the composition is either fully absorbable or partially absorbable. In other embodiments, the composition is not absorbable.

DETAILED DESCRIPTION OF THE INVENTION

The present invention provides curable, absorbable polyurethane and polyureaurethane compositions. The compositions are most often formed by combining an isocyanate or an isocyanate prepolymer of the invention with a polyol and/or a polyamine as described herein to form a polyurethane and/or polyurea-based polymer. In certain embodiments, the isocyanate and polyol are further combined with one or more chain extenders as described below. The combination results in a polymerization reaction that produces heat, but is generally less than 60° C. and no noxious fumes are released during or after mixing.

The compositions of the invention are biocompatible, fully or partially biodegradable are suitable for use in vivo, particularly in bone repair and replacement surgery, and especially for use as a bone cement, a bone substitute and/or a bone hemostatic agent. As used throughout the present specification, the term "biocompatible" refers to materials that do not induce undesirable side effects when administered or implanted in vivo. A biocompatible material may also be described herein as "nontoxic". As used throughout the present specification, the terms "degradable", "biodegradable", "resorbable", and "absorbable" are used interchangeably to refer to the ability of the claimed compositions to degrade (partially or completely) under physiological conditions into non-toxic products that can be metabolized or excreted within a period of time, generally several weeks up to a year or about 18 to 24 months or longer.

The polyurethane compositions of the invention are polymers or prepolymers formed from the reaction of (i) a degradable polyaromatic isocyanate, preferably a diisocyanate or a polyisocyanate, and (ii) a polyol and/or a polyamine, which may or may not be degradable, with the optional addition of (iii) a chain extender or curative, which may or may not be degradable. As used throughout the present specification, the terms "isocyanate" and "polyisocyanate" may be used interchangeably to refer to the polyaromatic isocyanates used in making the curable, absorbable polyurethanes of the invention. The term "polyisocyanate" encompasses a chemical structure having two or more isocyanate groups. The term "polyaromatic" refers to isocyanate groups residing on two or more aromatic rings. The term "polyol" encompasses a chemical structure having two or more hydroxyl groups. As used herein, the term "polyol" refers to both diols and polyols.

The polyaromatic isocyanates used to form the polyurethane compositions of the invention comprise at least one hydrolysable linkage bridging the aromatic rings. In certain embodiments, the hydrolysable linkage bridging the aromatic rings is derived from glycolic acid, lactic acid, caprolactone, or p-dioxanone. Suitable polyaromatic isocyantes are described in more detail below. The term "polyaromatic isocyanates" as used herein is meant to distinguish from aromatic isocyantes having only a single aromatic ring such as toluene diisocyante. The isocyanate, polyol, and chain extender components of the compositions of the invention, as well as other optional components, are described in more detail below.

The compositions of the invention are most often low-exotherm, biocompatible compositions suitable for use in vivo at least in that their formation does not produce toxic fumes or tissue-damaging amounts of heat and their degradation under physiological conditions does not produce toxic by-products and/or is not toxic to the implant recipient. In a preferred embodiment, the maximum exotherm of the polymerization reaction is 65° C. or less, and most preferably 50° C. or less.

In certain embodiments, the compositions are osteopromotive. As used throughout the present specification, the term "osteopromotive" encompasses the ability to support, enhance or accelerate the growth of new bone tissue by one or more of osteogenesis, osteoconduction, and/or osteoinduction. In certain embodiments, the compositions are also hemostatic. A hemostatic composition of the invention is able to be applied to the surface of bleeding bone in its uncured state, and stop the bleeding within a period of time. For example, the bleeding is stopped immediately after application of the composition or within about 1 minute, or within about 2-5 minutes, or within about 5-10 minutes. In preferred embodiments the hemostatic compositions are adhesive and capable of adhering to bone and/or soft tissue. Although the hemostasis is primarily mechanical (tamponade), in certain embodiments a hemostatic composition of the invention may also contain one or more agents that act as active chemical hemostats. Non-limiting examples include, blood clot-inducing agents such as prothrombin, thrombin, oxidized cellulose, microcrystalline collagen, fibrinogen, and fibrin. In one embodiment, the composition may also comprise one or more of epinephrine, tannic acid, ferrous sulfate, and the double-sulfates of a trivalent metal and a univalent metal such as potassium aluminum sulfate and ammonium aluminum sulfate. Thus, a composition of the invention in either its fluid, putty or solid form is also preferably hemostatic, mechanically or chemically, or by a combination of mechanical and chemical hemostasis. The term "fluid form" refers to the uncured form of the composition which is a viscous liquid or putty or which hardens or "cures" into the solid form.

The instant invention further provides self-setting (i.e., increased viscosity or hardening after mixing) compositions for medical use that are produced by mixing, kneading or combining together two or more individual putties. The individual component putties can be provided in sterile form, and may be hand mixed at the surgical table prior to implantation. Once mixed, the compositions disclosed herein are capable of hardening in the body and are particularly useful for orthopedic application as a hone hemostat, a hone adhesive, a hone void filler, or a hone cement. The compositions also can be used as soft tissue bulking agents, soft tissue hemostats, inhibitors of surgical adhesion formation, and as delivery vehicles for drugs and therapeutic agents.

The term "bone cement" is meant to distinguish certain embodiments of the invention from other embodiments, such as soft tissue adhesives, which may not possess mechanical properties suitable for use in bone repair. A bone cement composition of the invention when fully cured has a compressive strength, tensile strength, and elasticity suitable for use in bone repair or reconstruction. The solid form also bonds to bone or metal surfaces and reaches a self-supporting bond strength within about 90 minutes. In one embodiment, a fully cured composition of the invention has a compressive strength of from 30 to 150 MPa, or greater, a tensile strength of from 20 to 80 MPa, or greater, and an elasticity defined by a Modulus of Elasticity of from 1,400 to 1,800 MPa, or greater. In certain embodiments the compressive strength is at least 30 MPa, at least 40 MPa, at least 50 MPa, at least 60 MPa, at least 70 MPa, at least 80 MPa, or at least 100 MPa. In some embodiments, the compressive strength is greater than 100 MPa or greater than 150 MPa. In one embodiment, the compressive strength is between 100 and 150 MPa or between 150 and 200 MPa. Preferably, the solid form is sufficiently durable to be drillable or machinable. In certain embodiments the solid form has a tensile strength of at least 20 MPa, at least 30 MPa, at least 40 MPa, at least 50 MPa, at least 60 MPa, or at least 80 MPa. In certain embodiments the solid form has a Modulus of Elasticity of at least 1,400 MPa, at least 1,500 MPa, at least 1,600 MPa, or at least 1800 MPa. In one embodiment, the solid form has a compressive strength of at least 60 or 70 MPa, a tensile strength of at least 40 or 50 MPa, and an elasticity of at least 1,600 or 1,800 MPa. The mechanical properties described here refer to the properties of the polyurethane alone, without the addition of other, optional, materials which may further increase these physical properties, especially compressive strength. In one embodiment, the polyurethane compositions of the invention do not comprise an optional particulate material. In certain embodiments, the particulate material, if present, is present in an amount up to about 80% by weight of the composition.

The fully cured form of a composition of the invention is also referred to herein as the solid form of the composition. This is to distinguish from the fluid form which may be a putty and/or viscous liquid that hardens or "cures" into the solid form. In addition, in preferred embodiments the solid form bonds to bone or metal surfaces and reaches a self-supporting bond strength within about 90 minutes. The solid form further bonds with tensile and shear strength equal to normal bone within about 72 hours. A composition of the present invention hardens into its solid form at room temperature or at body temperature within about 5 to 90 minutes. In certain embodiments the composition hardens into its solid form in about 1.0, 20, 30, 40, 50, 60, 70, 80, or 90 minutes.

The fluid form of the compositions is a putty or viscous liquid which hardens or "cures" into the solid form. The fluid form is moldable or pliable and does not adhere appreciably to surgical gloves or instruments but adheres well to moist hone surfaces. The fluid form of the composition is also resistant to dislodgement by surgical irrigation at the application site. The fluid form is useful, for example, to fill a cavity in the bone, for injection through a syringe to the site of application, or for bone reconstruction. The fluid form of the compositions of the invention remains in a moldable state at room temperature for up to 120 minutes. In one embodiment, the composition remains in a moldable state for 10, 15, 20, 30, 40, 60, 80, 90, or 120 minutes. The rate of cure can be increased, for example, by the addition of a catalyst as described in more detail below. In addition, the aromatic isocyanate monomers described herein will react fastest with the polyamine component, then the polyol component and slowest with water. In addition, the rate of cure can be decreased, for example, by replacing one or more primary diols in the composition with secondary diols.

During the curing of a polyurethane formed from liquid components, the composition may undergo a transition to a "taffy" like state prior to fully setting. Such a "taffy" phase which may also be considered "putty-like" is distinguished from the component putties described herein. The component putties comprise particulate "fillers" to establish their "putty-like" characteristics.

The compositions of the invention are fully or partially degradable under physiological conditions within a period of time. Where the compositions are fully degradable, they are degraded within about 12 months. The degradation may be enzymatic or non-enzymatic or a combination of both. In one embodiment, the compositions of the invention are initially degradable into non-toxic products by a non-enzymatic hydrolysis under physiological conditions. In a preferred embodiment, the compositions are fully degradable within a period of time less than 12-24 months. In certain embodiments, the degradation time does not exceed 3 months or 6 months. In one embodiment, a composition of the invention is degradable within about 2 to 4 weeks after placement in vivo. In other embodiments, a composition of the invention is fully degradable within about 4 to 6 weeks, or within about 2 to 4 months, 4 to 6 months, 6 to 8 months, or 8 to 12 months. In certain embodiments, the compositions comprise components that are fully degradable or absorbable. In other embodiments, the compositions are comprised of components that are partially degradable or absorbable, or non-degradable. In certain embodiments, the compositions are formed from a combination of fully degradable, partially degradable, and non-degradable components.

The hydrolysable embodiments of the invention are degradable at least due to the presence of functional groups in the polymer chain that are readily hydrolysable under physiological conditions. Thus, the term "partially degradable" as used in the present specification encompasses the percentage of functional groups in the polymer chain that are hydrolyzed compared to the total number of hydrolysable groups. In this context, a partially degradable polyurethane of the invention encompasses compositions in which, after a suitable period of time, about 75% of the hydrolysable groups are hydrolyzed. In certain embodiments, a partially degradable compositions is one in which about 25% to 75% or 50% to 75% or about 75% to 90% of the hydrolysable groups are hydrolyzed. The rate of degradation of the polyurethane compositions of the invention can be controlled in order to provide compositions that degrade at a slower or faster rate, compared to a base composition. In general, the rate of degradation is controlled by varying the isocyanate and polyol/polyamine components of the compositions, as well as the optional chain extender component according to the following parameters. In one aspect, the rate of degradation is controlled by choice of the isocyanate. Generally, the more glycolide in the hydrolysable bridge, the faster it will degrade while more lactide in the hydrolysable bridge will degrade slower, and combinations of glycolide and lactide will degrade at intermediate rates. In another aspect, the rate of degradation is controlled by varying the hydrophobic/hydrophilic balance of the polyol/polyamine component. Generally, the more carbon atoms or methylene groups between the hydrolysable functions, the slower will be the hydrolysis. For example, ethylene glycol will provide a composition that hydrolyses more rapidly than, for example, propane diol, which in turn hydrolyses more rapidly than butane diol. In addition, the use of hydrolysable diamines as chain extenders will increase the rate of hydrolysis. In another aspect, copolymers of caprolactone and glycolide hydrolyze faster than copolymers of caprolactone and lactide and the addition of D, L-lactide also increases the rate of hydrolysis. Thus, for example, a bis-diphenyldiisocyanate bridged with a polyglycolide, a polyglycolide-co-lactide, a polylactide, a polycaprolactone-co-glycolide, a polycaprolactone-co-lactide, a polycaprolactone will hydrolyze at increasingly slower rates. For comparison, polyurethanes prepared using methylene bis-diphenyldiisocyanate, with no hydrolyzable linkages, are not significantly degradable under physiological conditions. In other embodiments, enzymatic sensitive sites such as di or polylysines or arginines are incorporated into one or more of the substituents.

In certain embodiments, the fully cured compositions of the invention have a certain defined pore size. Porosity is controlled through the inclusion of water, surfactants, and/or cell openers during the process of combining the one or more isocyanate components with the polyol/polyamine component to form the polyurethane compositions of the invention. For example, porosity may be controlled by the addition of a small amount of water to a prepolymer containing isocyanate groups. The water reacts with the isocyanate group to form carbon dioxide resulting in porosity. In one embodiment, the solid form has an average pore size in the range of from about 5 to 700 microns. In certain embodiments, the average pore size is from about 5 to 100 microns, from about 5 to 300 microns, from about 5 to 500 microns, and from about 5 to 700 microns. In certain embodiments, the average pore size is from about 100 to 300 microns, from about 200 to 500 microns, from about 300 to 600 microns, and from about 500 to 700 microns, or greater. In another embodiment, the solid form has an average pore size in the submicron range. In certain embodiments, the average pore size is from about 100 to 1000 nanometers, from about 100 to 400 nanometers, from about 400 to 800 nanometers, from about 200 to 600 nanometers, or from about 500 to 900 nanometers. Porosity may also be introduced into the cured polyurethanes through the use of porous filler materials (eg commercially available calcium phosphates with pore sizes of 200 microns or greater). This approach is particularly useful in the multi-putty embodiments.

The compositions of the invention are provided either in a fluid form or in the form of a binary composition of (1) one or more of the isocyanates of the invention and (2) at least one polyol. A chain extender may also be used, as described below. The binary composition may also comprise, e.g., a prepolymer and a chain extender. A prepolymer is a low molecular weight polymer having reactive end groups, e.g., hydroxyl groups. As used in this context, a low molecular polymer refers to a polymer having a number average molecular weight in the range of about 500 to 20,000 or 500 to 10,000. The prepolymer is formed, for example, from the initial reaction of the one or more isocyanates with the at least one polyol. Formation of a high molecular weight polymer is achieved by addition of the chain extender.

The compositions of the invention may also be provided as a package or article of manufacture containing a fluid form (which can, for example, be frozen to halt the curing process). In another embodiment, the compositions are provided as a binary package or article of manufacture containing in a first package a prepolymer of the isocyanate and the polyol/polyamine components and in the second package one or more chain extenders. The second package may also optionally contain a crosslinker. In another embodiment, the compositions are provided as a binary package or article of manufacture containing in a first package one or more polyaromatic di- or polyisocyanates as described herein and in a second package one or more of the polyol/polyamine components as described herein. A third package may optionally contain a chain extender or crosslinker. Generally, the amount of polyisocyanate (I) present in the first package is in excess of the amount of polyol and/or polyamine (H) in the second package. The amount of isocyanate (I) is the molar ratio of NCO groups to active hydrogen functional groups (H) (e.g., hydroxyl, amino, and mixtures thereof). Generally, the ratio of polyisocyanate to polyol/polyamine (I:H) is at least 2:1. In certain embodiments, the packages contain relative amounts of the isocyanate to diiol/polyol/polyamine (I:H) of about 1.5:1, about 2:1, about 3:1, or about 4:1. In other embodiments, the ratio is about 5:1, about 8:1, about 10:1, about 20:1, or about 50:1. In certain embodiments, a package or article of manufacture of the invention has a shelf life of at least 1-2 years. In certain embodiments, the package has a shelf life of 6 months, 12 months, 18 months, or 24 months. In certain embodiments the package is sterile or sterilizable, for example by irradiation or by autoclaving. In certain embodiments, the package further comprises a syringe.

As discussed above, some embodiments of the invention are bone cements or hemostatic agents and, as such, are required to have different mechanical properties compared to, e.g., soft tissue adhesives or hemostats. The compositions of the invention are intended to cure in situ, most often to bond to the surrounding bone. The cements of the invention will also bond, for example, to a metal plate or other surgically introduced article, if present. In contrast, pre-polymerized bone fillers are fully polymerized before placement into the body and are therefore incapable of bonding. Organic polymeric bone fillers are also generally porous composite materials containing, for example, a polymer matrix having a relatively high weight percent of particles embedded in the matrix. The particles serve to increase the compressive strength of the polymer and may also promote the growth of new bone (e.g., osteoblasts) into the matrix. The compositions of the invention may contain particulate materials, as described below, but generally such materials, if present, will be present in an amount of up to about 80% by weight of the composition. This is because such materials are not employed in the present compositions to increase the mechanical strength of the composition but instead for other purposes, such as, for example, to promote the growth of bone into the site. Thus, in some embodiments, the compositions of the invention further comprise an optional particulate material. In one embodiment, the particulate material is a carbonate, e.g., calcium carbonate, magnesium carbonate, aluminum carbonate, iron carbonate, zinc carbonate, calcium bicarbonate, and sodium bicarbonate. In other embodiments, the particulate material is a ceramic such as substituted or augmented calcium phosphate (e.g, silicate, strontium or magnesium substitution) or a glass such as bioglass. In some embodiments, the particulate material is one or more of calcium sulfate, calcium phosphosilicate, sodium phosphate, calcium aluminate, calcium phosphate, hydroxyapatite, demineralized bone, or mineralized bone. Preferably, if included in the compositions of the invention, such particulate materials (including e.g., carbonates, ceramics, glasses, etc.) form up to about 80% by weight of the fully cured composition.

Optionally, the process may also comprise the inclusion of a surfactant, at least one radiopaque substance, or at least one protein, or any combination of the foregoing.

The process may further comprise the inclusion of one or more cross-linkers. In one embodiment, the one or more cross-linkers is selected from glycerol and pentaerythritol. In one embodiment, the cross-linker is a trifunctional castor-oil based polyol.

In certain embodiments, the process further comprises the inclusion of one or more of bone, demineralized bone matrix, bone morphogenetic protein, calcium phosphate, siliconized calcium phosphate, calcium pyrophosphate, hydroxyapatite, poly methyl methacrylate, glass-ionomer, absorbable phosphate glass, calcium sulfate, or tricalcium phosphate, bone-like mineral (e.g., crystalline hydroxyapatite or calcium pyrophosphate).

In one embodiment, the compositions of the invention are formed by a process of combining an isocyanate prepolymer with a polyol or chain-extender, and a catalyst, optionally with one or more particulate materials as described above, to form a poly(urethane-isocyanurate) composition. In another embodiment, the isocyanate prepolymer is combined with a polyol, water, and a catalyst, optionally with an osteoconductive filler, to form a poly(urethane-urea-isocyanurate) composition.

In one embodiment, the curable, absorbable polyurethane compositions of the invention comprise a glycolide-linked polyaromatic diisocyanate and a polycaprolactone-co-glycolide polyol. It should be understood that the compositions of the invention are formed from the reaction of a polyaromatic polyisocyanate, one or more polyols and/or polyamines and, optionally, a polyol and/or a polyamine as a chain extender. Thus, in this context, and as used throughout the present disclosure with respect to the compositions of the invention, the term "comprises" refers to the polyurethane or polyureaurethane reaction product of an isocyanate, a polyol/polyamine and, optionally, a polyol and/or a polyamine as a chain extender. In one embodiment, the composition further comprises butanediol, e.g., as a chain extender. In one embodiment, the composition further comprises one or more of water, a carboxylic acid, e.g., benzoic acid (as a foaming agent), a divalent or polyvalent metal salt, a metal carbonate or bicarbonate, or a phosphate, e.g., for osteoconductivity. In one embodiment, the glycolide-linked diisocyanate monomer has the following structure:

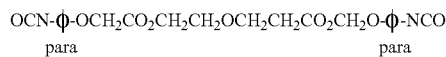
para    para

In one embodiment, the polycaprolactone-co-glycolide polyol has the following structure:

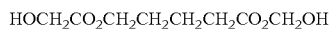

In one embodiment, the curable, absorbable polyurethane compositions of the invention comprise a lactide linked diisocyanate and a polycaprolactone-co-lactide polyol. In one embodiment, the composition further comprises butanediol, e.g., as a chain extender. In one embodiment, the composition further comprises one or more of water, a carboxylic acid, e.g., benzoic acid (as a foaming agent), a divalent or polyvalent metal salt, a metal carbonate or bicarbonate, or a phosphate, e.g., for osteoconductivity. In one embodiment, the lactide-linked diisocyanate monomer has the following structure:

para    para

In one embodiment, the polycaprolactone-co-lactide polyol has the following structure:

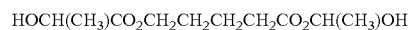

In one embodiment, the curable, absorbable polyurethane compositions of the invention comprise a tetraisocyanate. In one embodiment, the tetraisocyanate is a caprolactone ethylene glycol linked phenylalanine diisocyanate. This may be reacted with the tetra-amine precursor of the tetraisocyanate described above. In one embodiment, the composition further comprises one or more of water, a carboxylic acid, e.g., benzoic acid (as a foaming agent), a divalent or polyvalent metal salt, a metal carbonate or bicarbonate, or a phosphate, e.g., for osteoconductivity.

The Isocyanate Component

The absorbable polyurethane compositions of the invention are prepared from one or more polyaromatic di- or polyisocyanates having at least one hydrolysable linkage bridging at least two of the aromatic rings. In certain embodiments, the hydrolysable linkage bridging the aromatic rings is derived from glycolic acid, lactic acid, caprolactone, or p-dioxanone. In most cases, the hydrolyzable linkage is an ester which may degrade into an acid and an alcohol as a result of exposure to water or to naturally occurring esterases. Amide linkages are usually more difficult to hydrolyze than esters. Another option is the easily hydrolyzable acid anhydride linkage. Sulfonamides may also be considered in this context. The polyaromatic di- or polyisocyanates described herein are distinct from isocyanates having only a single aromatic ring such as toluene diisocyante, methylene bis-p-phenyl diisocyanate, and aromatic polyisocyanates generally.

Suitable isocyanates for use in making the compositions of the invention are described in U.S. Pat. No. 7,772,352 and U.S. Patent Application Serial No. 2009/0292029, each of which is incorporated herein by reference.

In certain embodiments, an absorbable polyurethane composition of the invention is prepared from one or more aromatic isocyanates selected from the following formulas I, II, III, IV, and V:

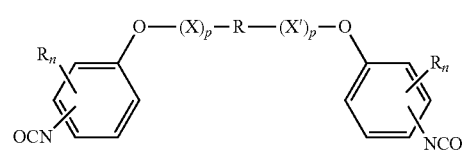

-continued

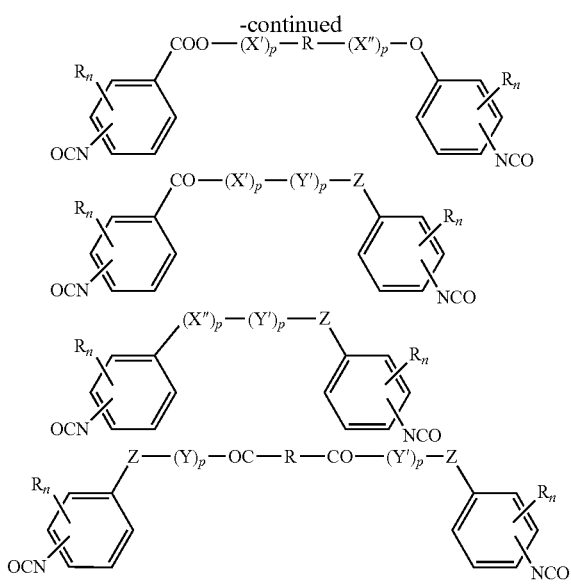

wherein
each X represents a member independently selected from:
—CH$_2$COO— (glycolic acid moiety),
—CH(CH$_3$)COO— (lactic acid moiety),
—CH$_2$CH$_2$OCH$_2$COO— (dioxanone moiety),
—CH$_2$CH$_2$CH$_2$CH$_2$CH$_2$COO— (caprolactone moiety),
—(CH$_2$)$_y$COO— where y is one of the numbers 2, 3, 4 or 6-24 inclusive, and
—(CH$_2$CH$_2$O)$_{z'}$CH$_2$COO— where z' is an integer between 2 and 24, inclusive;
each X' represents a member independently selected from:
—OOCH$_2$— (glycolic ester moiety),
—OOC(CH$_3$)CH— (lactic ester moiety),
—OOCCH$_2$OCH$_2$CH$_2$— (dioxanone ester moiety),
—OOCH$_2$CH$_2$CH$_2$CH$_2$CH$_2$— (caprolactone ester moiety),
—OOC(CH$_2$)$_y$— where y is one of the numbers 2, 3, 4 or 6-24 inclusive, and
—OOCCH$_2$(OCH$_2$CH$_2$)$_{z'}$— where z' is an integer between 2 and 24, inclusive;
each X" represents a member independently selected from:
—OCH$_2$CO— (glycolic acid moiety),
—OCH(CH$_3$)CO— (lactic acid moiety),
—OCH$_2$CH$_2$OCH$_2$CO— (dioxanone moiety),
—OCH$_2$CH$_2$CH$_2$CH$_2$CH$_2$CO— (caprolactone moiety),
—O(CH$_2$)$_y$CO— where y is one of the numbers 2, 3, 4 or 6-24 inclusive, and
—O(CH$_2$CH$_2$O)$_{z'}$CH$_2$CO— where z' is an integer between 2 and 24, inclusive;
each Y represents a member independently selected from:
—COCH$_2$O— (glycolic ester moiety),
—COCH(CH$_3$)O— (lactic ester moiety),
—COCCH$_2$OCH$_2$CH$_2$O— (dioxanone ester moiety),
—COCH$_2$CH$_2$CH$_2$CH$_2$CH$_2$O— (caprolactone ester moiety),
—CO(CH$_2$)$_m$O— where m is an integer between 2-4 or 6-24 inclusive, and
—COCH$_2$O(CH$_2$CH$_2$O)$_n$— where n is an integer between 2 and 24, inclusive;
each Y' represents a member independently selected from:
—OCH$_2$OC— (glycolic ester moiety),
—O(CH$_3$)CHOC— (lactic ester moiety),
—OCH$_2$CH$_2$OCH$_2$OC— (dioxanone ester moiety),
—OCH$_2$CH$_2$CH$_2$CH$_2$CH$_2$OC— (caprolactone ester moiety),
—O(CH$_2$)$_m$OC— where m is an integer between 2-4 or 6-24 inclusive, and
—(OCH$_2$CH$_2$)$_n$OCH$_2$OC— where n is an integer between 2 and 24, inclusive;
each R is a benzyl or an alkyl group, the alkyl group being either straight-chained or branched;
each p is independently an integer between 1 and 4, inclusive;
Z is O or NH; and
Rn represents one or more members selected from H, alkoxy, benzyloxy, aldehyde, halogen, carboxylic acid and —NO$_2$, which is attached directly to an aromatic ring or attached through an aliphatic chain. The aromatic compound is selected from amine and/or carboxylic acid containing phenols, such as amino-phenols, amino-salicylic acids and amino-benzoic acids.

In other embodiments, an absorbable polyurethane composition of the invention is prepared from one or more aromatic isocyanates selected from the following formula VI:

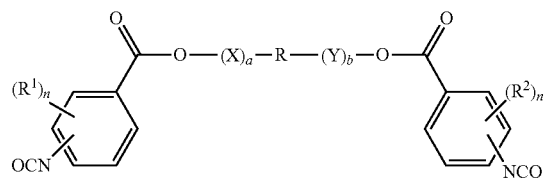

wherein:
R is alkylene-[C(R$^4$)(R$^5$)]$_s$-alkylene-, wherein (1) one or more of the —CH$_2$— moieties in one or more alkylene chain portions of R are optionally replaced by O or S; or (2) one or more of the —CH$_2$CH$_2$— moieties in the alkylene chain portions of R are optionally replaced by —C(=O)O or OC(=O);
each R$^1$ is independently [C(R$^2$)(R$^3$)]$_p$Z;
each Z is independently alkoxy, aralkyloxy, C(=O)H, halogen, C(=O)OH, or NO$_2$;
each R$^2$ and R$^3$ is independently H or alkyl;
R$^4$ is H, OR$^6$ or CH$_2$OR;
R$^5$ is H or CH$_2$OR;
each R$^6$ is independently:

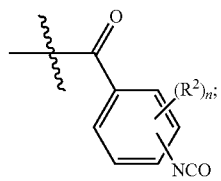

each X is independently CH(CH$_3$)C(=O)O, (CH$_2$)$_y$, C(=O)O, or (CH$_2$CH$_2$O)$_z$CH$_2$C(=O)O;
each X is independently OC(=O)CHCH$_3$, OC(=O)(CH$_2$)$_y$, or OC(=O)CH$_2$(OCH$_2$CH$_2$)$_z$;
each a and b is independently an integer from 1 to 6;
n is an integer from 0 to 4;
p is an integer from 0 to 10;
s is the integer 0 or 1; and
each y and z is independently an integer from 1 to 24.

In a particular embodiment, an absorbable polyurethane composition of the invention is prepared from one or more aromatic isocyanates selected from the following compounds, 1-12:
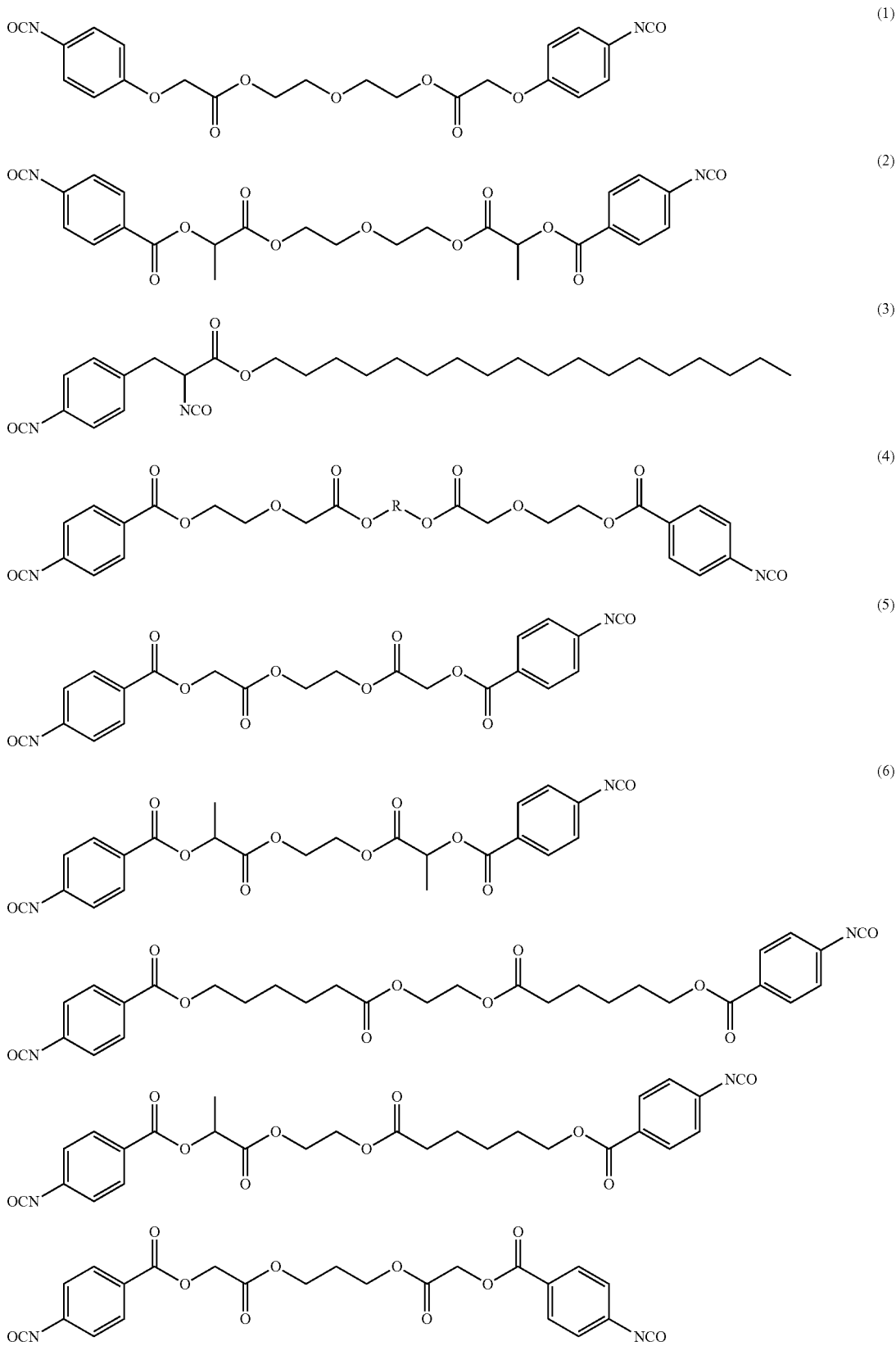

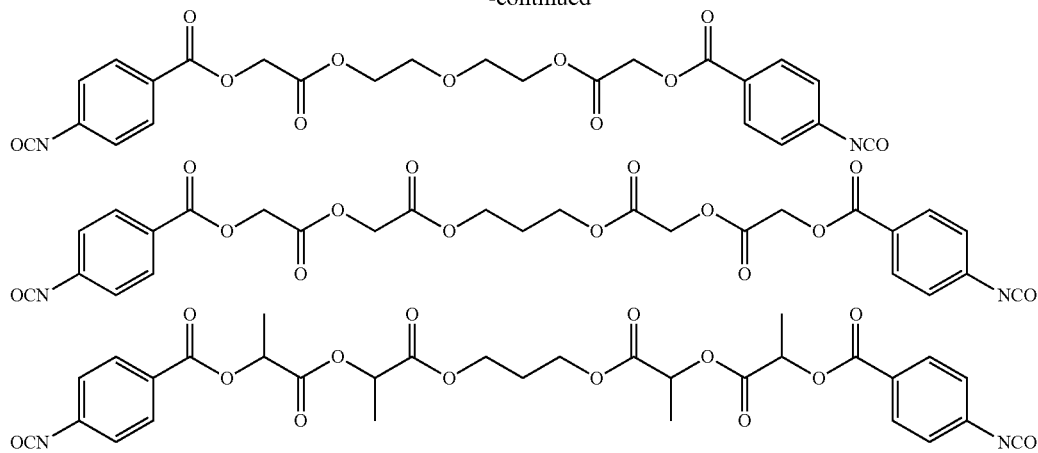

The Isocyanate Component of the Multi-Putty Embodiment

Any of the di- or polyisocyanates discussed above are preferred for the multi-putty embodiments. In certain embodiments, the isocyanate is an aromatic isocyanate, an aliphatic isocyanate, a cycloaliphatic isocyanate, or an adduct of an isocyanate. Examples of suitable adducts of isocyanate include a hexamethylene diisocyanate trimer (DESMODUR N-3390) and a hexamethylene diisocyanate biuret (DESMODUR N-100) both commercially available from Bayer AG. An example of a suitable aromatic isocyanate is diphenylmethanediisocyanate, also known as "MDI." Commercially available examples of diphenylmethanediisocyanate include mixtures of 2,4-diphenylmethane diisocyanate and 4,4-diphenylmethanediisocyanate isomers (ISONATE 50 OP, Dow Chemical Co. and RUBINATE 9433, Huntsman Corp.). Diphenylmethanediisocyanate is also commercially available in its pure 4,4-diphenylmethanediisocyanate form (MONDUR M, Bayer AG and RUBINATE 44, Huntsman Corp.). Other examples of suitable aromatic isocyanates include the commercially available polymeric isocyanates ISONATE 143L, ISONATE PAPI 901, and ISONATE PAPI 27 (Dow Chemical Co.). These diisocyanates, particularly the diphenylmethane derivatives, generally result in non-absorbable or slowly absorbable polyurethanes. A preferred isocyanate is [5-[2-[2-(4-Isocyanatobenzoyl)oxypropanoyloxy]-ethoxy]-1-methyl-2-oxopentyl]-4-isocyanatobenzoate, or "ALD", which is readily hydrolysable.

The Polyol/Polyamine Component

The diols, polyols, and polyamines suitable for use in forming the polyurethane and polyureaurethane compositions of the invention are either degradable or non-degradable, or a mixture of the two. As used herein, the term "polyol" is meant to refer generically to diols and polyols, unless indicated otherwise. Generally, the compositions of the invention are formed by the combination of an excess of the isocyante component with the polyol/polyamine component. The relative amounts are calculated as the molar ratio of NCO groups of the isocyanate component (I) to the active hydrogen functional groups (H) (e.g., hydroxyl, amino, and mixtures thereof) of the polyol/polyamine component. Generally, the ratio of polyisocyanate to polyol/polyamine (I:H) is at least 2:1. In certain embodiments, the ratio is about 1.5:1, about 2:1, about 3:1, or about 4:1. In other embodiments, the ratio is about 5:1, about 8:1, about 10:1, about 20:1, or about 50:1.

In certain embodiments, the polyol/polyamine component is present in an isocyanate prepolymer in an amount of from about 5% to about 50% by weight of the prepolymer. In certain embodiments, the polyol/polyamine component is present in an amount of from about 5% to 10%, from about 10% to 20%, from about 20% to 35%, from about 25% to 40%, or from about 35% to 50% by weight of the prepolymer.

Polyols suitable for use in the present invention include biocompatible naturally occurring polyols, synthetic polyols, and mixtures thereof. In certain embodiments, the polyols comprise at least one ester group. In certain embodiments, the polyol comprises 2 to 4 ester groups or 5 to 10 ester groups. Preferably, the polyol has two or more hydroxyl groups. Suitable polyols include diols and polydiols having repeating units containing up to about 18 carbon atoms. Examples of suitable diols include 1,2-ethanediol (ethylene glycol), 1,2-propanediol (propylene glycol), 1,3-propanediol, 1,4-butanediol, 1,5-pentanediol, 1,3-cyclopentanediol, 1,6-hexanediol, 1,8-octanediol and combinations thereof. Examples of preferred polydiols include polyethylene glycol with molecular weights of from about 500 to about 10000, polytetramethylene ether glycols, polyols derived from glycolide, lactide, trimethylenecarbonate, p-dioxanone and/or caprolactone with molecular weights of about 500 to about 10000.

In one embodiment, the polyol is a synthetic polyol selected from a polycaprolactone polyol, polyester polyols, polyadipate polyols (e.g., poly(hexane-adipate) diol, poly(butane-adipate) diol, poly(ethylene/propylene-adipate) diol, poly(hexane/adipate/isophthalate diol)), and polyols that have been derived from a synthetic acid (e.g., isophthalic acid, maleic acid). An example of a suitable biocompatible synthetic polyol is a polycaprolactone diol that is commercially available from Dow Chemical under the trade name TONE 32 B8. a polycaprolactone co-glycolide or a polycaprolactone co-lactide. Further non-limiting examples of suitable synthetic polyols include poly(oxypropylene) glycols, poly(oxytetramethylene) glycols, and poly-oxyethylene) glycols. In one embodiment, the synthetic polyol is selected from a polycaprolactone co-glycolide or a polycaprolactone co-lactide.

In one embodiment, the polyol is a naturally occurring polyol selected from castor oil, safflower oil, lesquerella oil, the polyols that may be obtained by chemical modification of naturally occurring vegetable oils (e.g., castor oil, olive oil, sesame oil, corn oil), naturally occurring oils that have been trans-esterified (e.g., a modified castor oil polyol that has been prepared by the transesterification reaction of natural castor oil with suitable crosslinkers (e.g., glycerol, trimethylolpropane, and the like) or with acids such as adipic acid), and naturally occurring oils that have been hydrogenated. Further non-limiting examples of suitable naturally occurring polyols include the commercially available castor-oil-based polyols CASPOL5001, CASPOL1962, and CASPOL5004 (all available from CasChem, Inc.). In certain embodiments, the polyol is not a naturally occurring polyol such as castor oil, safflower oil, lesquerella oil.

In certain embodiments, an isocyanate prepolymer is combined with a polyamine to form a poly(urethane-urea). The polyamine may be a primary or secondary di-amine, or a hindered amine. Non-limiting examples of suitable polyamines include, hindered diamine (e.g., isophorone diamine, "IPDA"), 1,4-cyclohexyl diamine, 1,3-pentane diamine, and aliphatic secondary diamines, and mixtures thereof. In certain embodiments of the present invention, aliphatic diamines and cycloaliphatic diamines may be particularly suitable, and may offer improved biocompatibility. Commercially available examples of suitable polyamines include CLEARLINK 1000 (Dorf Ketal).

Amines including diamines that may be suitable for use in the preparation of polyurea and polyureaurethanes include but are not limited to polyethyleneimines, PEG amines with weight average molecular weights from about 500 to about 5,000, polyoxypropylenediamines available under the tradename JEFFAMINES (Huntsman Corporation, Houston, Tex.), spermine, spermidine, hexamethylenediamine, octamethylenediamine, decamethylenediamine, dodecamethylenediamine, hexadecamethylenediamine, octadecamethylenediamine, polyamidoamine dendrimers, dextrans, PEG-dextran conjugates, cysteines, proteins containing amines, non-biologically active symmetrical and unsymmetrical diamino compounds containing saturated and unsaturated, substituted and unsubstituted alkyl, aryl and alkylaryl groups having from about 2 to about 18 carbon atoms and hydrolysable diamines having the following formulas:

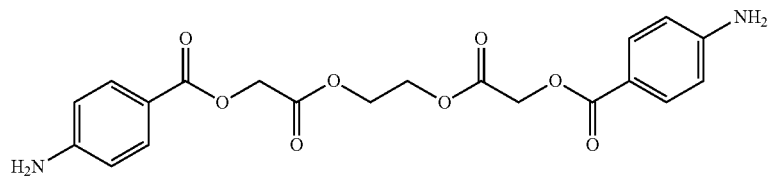

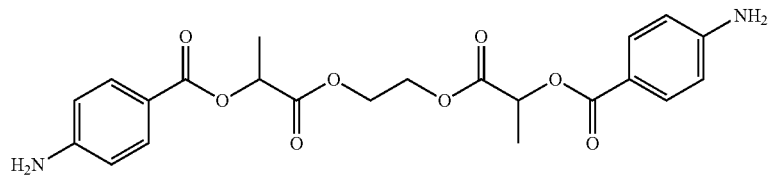

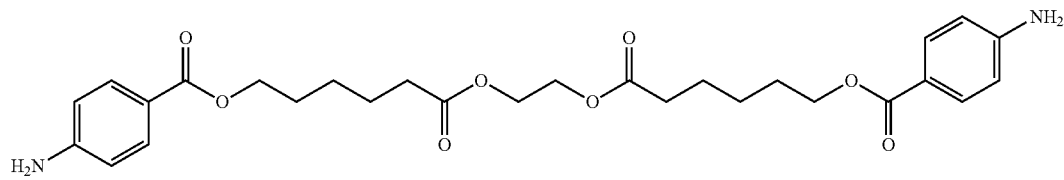

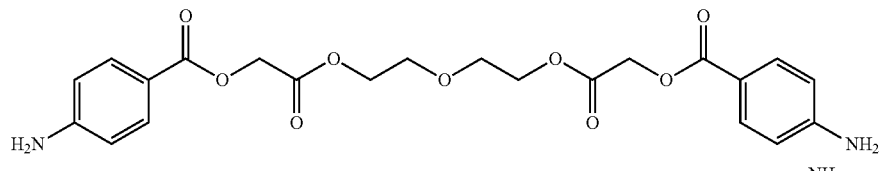

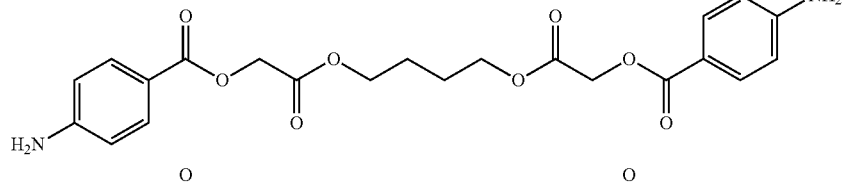

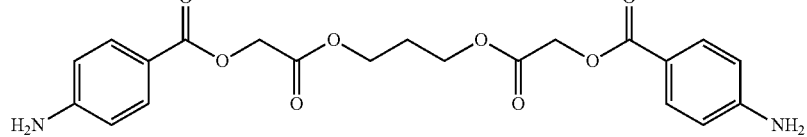

-continued

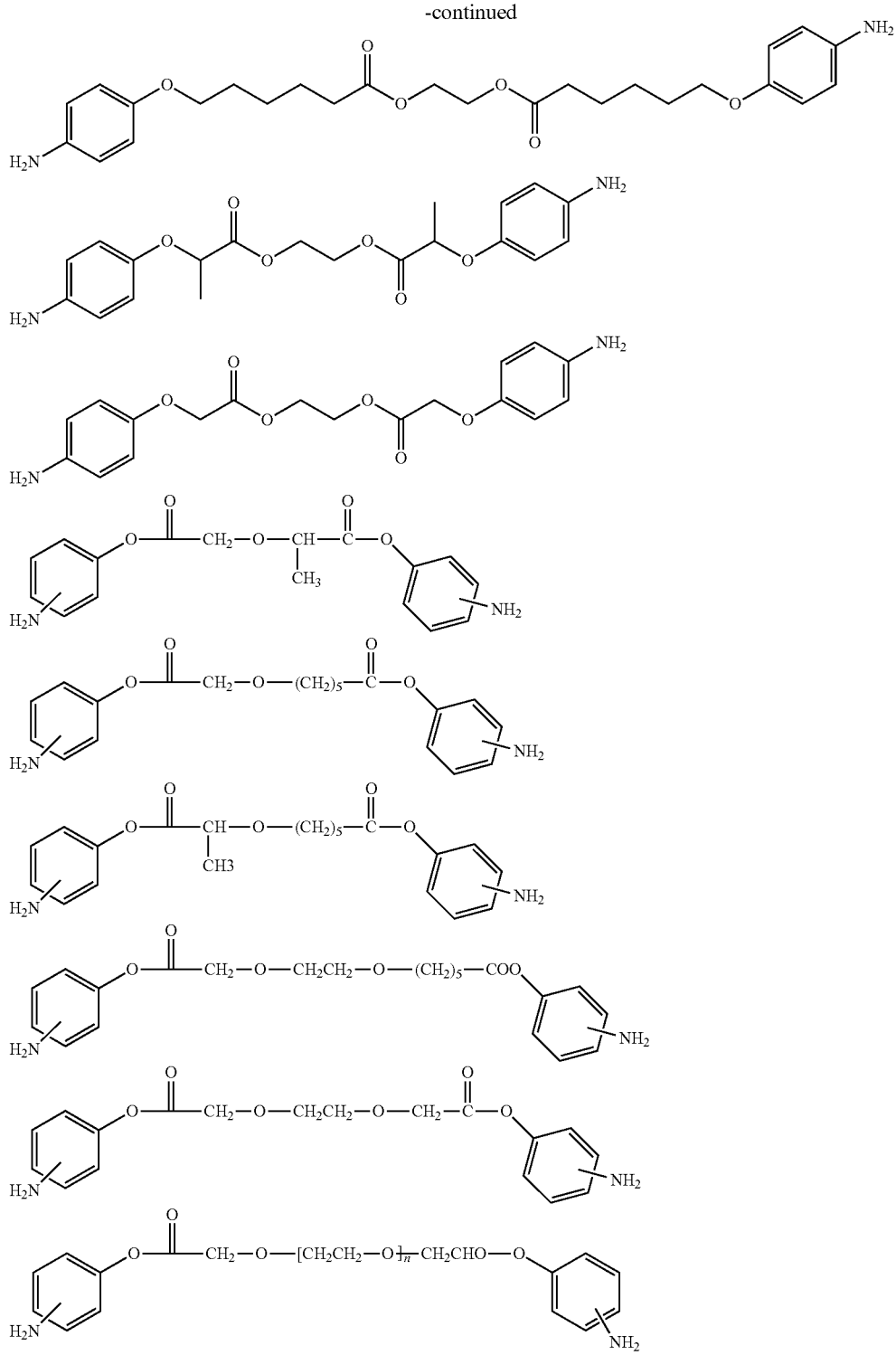

n = 10 to 12

The Polyol/Polyamine Component for the Multi-Putty Embodiment

Polyols suitable for use in the multi-putties disclosed herein include any of the biocompatible naturally occurring polyols, synthetic polyols, and mixtures thereof disclosed herein. In certain embodiments, the polyols comprise at least one ester group. In certain embodiments, the polyol comprises 2 to 4 ester groups or 5 to 10 ester groups. Suitable polyols have at least two hydroxyl groups. In certain embodiments, the polyol has three or more hydroxyl groups.

The Chain-Extender/Crosslinker Component

In certain embodiments, one or more optional chain extenders or crosslinkers is incorporated in the formation of the compositions of the invention. In certain embodiments, only a chain extender is present. In other embodiments, both a chain extender and a crosslinker is present. In one embodiment, the one or more chain extenders is a low molecular weight hydroxyl- and/or amine-terminated compound having a molecular weight in the range of 10 to 500 Daltons and a functionality of at least two. In one embodiment, the one or more chain extenders has a functionality of one or two. In certain embodiments, the chain extender is a short-chain diol or diamine. In a particular embodiment, the chain extender is selected from glycerol, 1,4 butanediol, 1,6-hexanediol, diethylene glycol, and combinations thereof. Chain extenders having a functionality of three or more than three are also referred to as crosslinkers. In certain embodiments, the compositions of the invention are formed without crosslinkers and the compositions of the invention are not crosslinked. In other embodiments, the compositions of the invention are formed with one or more crosslinkers. The degree of crosslinking can be controlled, for example, by varying the amount of crosslinker present.

In certain embodiments, the chain-extender or crosslinker is present in an isocyanate prepolymer in an amount in the range of about 5% to about 80% by weight of the isocyanate prepolymer. In certain embodiments, the chain-extender or crosslinker is present in an amount of from about 5% to 20%, about 20% to 30%, about 30% to 40%, about 40% to 50%, about 50% to 60%, from about 60% to 70%, or from about 70% to 80% by weight of the isocyanate prepolymer.

The chain extender for use in accordance with the invention may be degradable or non-degradable. Preferably, at least one degradable chain extender is used. Suitable degradable chain extenders for use in the present invention are described in U.S. patent application Ser. No. 2009/0082540, which is incorporated herein by reference. In one embodiment, the at least one degradable chain extender is $HOCH_2CO_2CH_2CH_2OH$ or $HOCH_2CO_2CH_2CH_2O_2CCH_2OH$.

Other suitable chain-extenders or crosslinkers include a natural or synthetic aliphatic polyols. Suitable polydiols for use in the present invention include diol or diol repeating units with up to 8 carbon atoms. Non-limiting examples include 1,2-ethanediol (ethylene glycol), 1,2-propanediol (propylene glycol), 1,3-propanediol, 1,4-butanediol, 1,5-pentanediol, 1,3-cyclopentanediol, 1,6-hexanediol, 1,4-cyclohexanediol, 1,8-octanediol and combinations thereof.

In other embodiments, the chain extender is a polyol selected from polyethylene glycol and polypropylene glycol having molecular weights of 500-10000 Daltons. Other examples include CASPOL1962 and CASPOL5004. In certain embodiments the preferred polydiols include polydiols selected from polyethylene glycol and polypropylene glycol with molecular weights of 500-10000. In some embodiments, the crosslinker is a non-absorbable crosslinker selected from triethanolamine (TEA), trimethylolpropane, and QUADROL (BASF Corp.). In some embodiments, the chain-extender is a non-absorbable chain extender selected from 1,4-butanediol, 1,6-hexanediol, and diethylene glycol. The chain-extender or crosslinker may be present in an isocyanate prepolymer in an amount in the range of about 10% to about 80% by weight of the isocyanate prepolymer.

In another embodiment, the dual putty system has improved setting and adhesiveness in aqueous environments. By nature, the isocyanate component, even containing hydrolysable linkages, is essentially hydrophobic and will resist dissolution in aqueous systems. However, many of the diols, e.g., diethylene glycol and chain extenders, e.g., butanediol are not resistant to water. This is true for diamines in this context. It has been found that making the diol more hydrophobic by adding a hydrophobic hydrocarbon-rich residue to a polyol, e.g., glyceryl-1 or 2-monostearate, a water resistant system is obtained. A variation of this embodiment involves the substitution of a silicon-based moiety for the hydrocarbon-rich residue. Alternatively hydrophobicity and setting rate in aqueous environments can be improved through the use of hydrophobic fillers such as insoluble or weakly soluble aliphatic molecules and salts thereof, including divalent salts, (eg calcium, magnesium, or zinc) of fatty acids. Also useful are cholesterol and its derivatives, as well as silated derivatives of ceramics or bone (Shimp et al., U.S. Pat. No. 7,270,813) Another embodiment of a water resistant, settable, dual putty system adds a small amount of hydrophobic isocyanate to the relatively hydrophilic polyol component resulting in a water-resistant mixture of polyol containing a minor amount of hydrophobic polyurethane prepolymer.

In one embodiment, the chain extender does not comprise an amino acid group.

Multi-Putty Embodiment

In one embodiment, the chain extender does not comprise an amino acid group.

The polyurethane reactants and reactions described above may be applied directly to the multi-putty embodiment of the invention. In this embodiment, the compositions are produced by mixing a first putty composition (e.g., "Component Putty A"), which comprises one or more reactants capable of participating in chemical reactions with one or more reactants present in a second putty composition (e.g., "Component Putty B"), and optionally, with reactive third, fourth, fifth, or more reactants in any number of additional putties (e.g., a third putty composition, a fourth composition, a fifth putty composition, or any number as deemed necessary or useful to those skilled in the art, to produce a product that is harder, less flowable, and/or more cohesive than the individual component putties. Individual component putties may be formed by preparing a suspension of a particulate within a liquid, but may also be comprised of one or more moldable solids, e.g., a wax-like material, a particulate solid, e.g., modeling clay combined with a moldable solid and/or a moldable solid and a liquid.

The multi-putty compositions are formed by chemical reactions which produce a self-hardening or increased viscosity polymer from two or more reactants (key reactive components), wherein the reactions are initiated when the two or more individual component putties are mixed or combined. Mixing results in hardening or increased viscosity of the product. In addition to the polyurethane reactions disclosed herein other polymeric reactions which may be applied to the multi-putty concept include epoxy reactions, and vinyl reactions. An epoxy adhesive or cement may be prepared by reacting a di-epoxide with an amine, such as a polyamine. Vinyl compounds, such as methylmethacrylate, may be prepared by reacting molecules containing a vinyl or alkene group with benzoyl peroxide (radical induction) or ferric chloride (ionic induction).

For any of the reaction chemistries, of which polyurethanes are the preferred embodiment, reactive components may be introduced in particulate form. In such situations, the reactive components also provide a bulking feature to the putty. The vehicle for the putty, in such instances, may be non-reactive and could include any material that does not detrimentally affect the reaction between the reactive components (and/or second putty). Reactive components may also be introduced as liquid vehicles. The reactive components for the component putties will generally be in liquid form, often as a viscous liquid.

One or more of the individual component putties may be prepared as a suspension. In suspension form, particles are mixed with a liquid vehicle in proportions sufficient to produce a formable putty. The particles of the suspension will generally be less than 50, 40, 30 or 25 microns (μm). Preferably, particles will be less than 15 microns, particle sizes of less than 10 microns, and nano particles are often particularly preferred. The particles within the suspension may be insoluble in the vehicle or the vehicle will be saturated with a soluble form of the particulate phase so that the particles themselves will not dissolve in the vehicle. Particles and liquid vehicles having similar hydrophilicity or hydrophobicity may be used in ratios of up to 80% of particle to vehicle (wt/wt). Other formulations useful to prepare a moldable suspension may require as little as 70, 60 or 50% particles. Some may employ 45% particles or less. The reactive molecules within the individual component putties may be present either in particulate or vehicle form, depending on the chemistry involved.

When the chemistry permits, one or more of the individual component putty compositions may be prepared as a moldable solid. Such solids, by themselves, have the moldability and texture of waxes, clays or soft plastics. In some cases, a softener (e.g., a non-reactive surfactant) may be included to achieve the desired moldability and to allow adequate mixing with other component putties. In instances where the reactive components can be prepared as a particulate solid, it may be blended with a liquid or a wax-like formable material to produce the individual component putty. Likewise, if the reactive components are prepared as moldable solids, they may be softened with a liquid vehicle.

In general, the individual putty compositions of the invention may be formed by a process of combining the inventive polyol and/or a polyamine components and an isocyanate or an isocyanate prepolymer component to form polyurethane and/or polyurea-based compositions. The combination results in a polymerization reaction that produces heat, but the incorporation of solids and/or fillers can serve as a heat sink to produce a modulated exotherm. No adverse fumes are released during or after mixing. The polyol component is a biocompatible, naturally-occurring or synthetic polyol, or a combination of the two, as described elsewhere herein. The isocyanate component is preferably a hydrolysable diisocyanate. The process may further comprise combining the polyol/polyamine and isocyanate components with either water or a carboxylic acid to form carbon dioxide thus making the polymer porous.

When one or more reactive components are liquids or formable solids, it may be desirable to mix it with an additive in the form of a particulate filler in order to produce useful putties. In addition to viscosity adjustment, additives may be employed to affect specific features of the component putty, the final product compositions described herein or the setting or cured polymer. Properties which may be affected include, but are not limited to, component putty softness and mixability; final product composition setting time, or softness (e.g., moldability), polymerized product tissue adherence, prevention of adhesion formation, osteoconductivity, osteoinductivity, inflammation, absorption, drug delivery properties and time, among others. In some embodiments, the reactive components are pre-reacted to produce polymerized or partially polymerized product. This material is then reduced to particulate form through standard methods such as cryo-milling. These particles of pre-reacted polymer may then be used as all or a portion of the particulate material.

Any of the additives described herein may be added in the role of a filler to produce a putty. For bone applications, calcium salts are preferred including calcium salts of fatty acids, phospholipids, calcium carbonate, calcium sulfates, and calcium phosphates. Other fillers, such as ceramics, glasses, Bioglasses, phosphate glasses, starches, cholesterols, binders, etc., may be employed. The reactive components for the component putties may also be present in the form of moldable solids such as waxes composed of fatty alcohol esters or polymers such as polyethylene glycol).

For example, the process may comprise the inclusion of an osteoconductive additive such as a carbonate, e.g., calcium carbonate, magnesium carbonate, aluminum carbonate, iron carbonate, zinc carbonate, calcium bicarbonate, and sodium bicarbonate. Other osteoconductive materials include ceramics such as substituted calcium phosphates (e.g, silicate, strontium or magnesium substitution) and glasses such as Bioglass. Optionally, the process may also comprise the inclusion of a surfactant, at least one radiopaque substance, or at least one protein, or any combination of the foregoing. The process may further comprise the inclusion of a cross-linker. In one embodiment, the cross-linker is a trifunctional castor oil-based polyol. In certain embodiments, the process further comprises the inclusion of one or more of bone, demineralized bone matrix, hone morphogenetic protein, calcium phosphate, siliconized calcium phosphate, calcium pyrophosphate, hydroxyapatite, poly methylmethacrylate, glass-ionomer, absorbable phosphate glass, calcium sulfate, or tricalcium phosphate, bone-like mineral (e.g., crystalline hydroxyapatite or calcium pyrophosphate). In one embodiment, the compositions of the invention are formed by a process of combining an isocyanate prepolymer with a polyol or chain-extender, and a catalyst, optionally with an osteoconductive filler, to form a poly(urethane-isocyanurate) composition. In another embodiment, the isocyanate prepolymer is combined with a polyol, water, and a catalyst, optionally with an osteoconductive filler, to form a poly(urethane-urea-isocyanurate) composition.

Component Putty Viscosity

Generally, compositions having a putty-like consistency may be achieved by appropriate adjustment of the liquid to solid ratio. Particle size may also be varied, with smaller particle sizes yielding smoother more cohesive putties. Alternatively or additionally, reactive components which are liquids and/or powders may be partially reacted by limiting one or more of the reactants to produce more viscous versions of the liquid components. Softeners such as non-reactive surfactants, hydrophilic polymers such as polyethylene glycol alkyl ether, etc., may also be added.

When one or more reactive components are particulate solids, it may be desirable to mix it with a liquid or moldable solid in order to produce a useful putty. There are also instances independent of the physical nature of the reactive components, where further adjustment of viscosity is required. In these instances, it is acceptable to add additional liquid. In addition to viscosity adjustment, vehicles may be employed to affect specific features of the component putties, final product composition, or the setting or cured polymer. Properties which may be affected include, without limitation, component putty softness and mixability, final product composition setting time or softness (e.g., moldability), polymerized product tissue adherence, prevention of tissue adhesion formation, osteoconductivity, osteoinductivity, inflammation, absorption, drug delivery properties, and time among others.

Osteoconductive Additives and Filler Materials

Non-limiting examples of osteoconductive additives that may be included in the compositions of the invention include a carbonate (e.g., calcium carbonate, magnesium carbonate, aluminum carbonate, iron carbonate, zinc carbonate, calcium bicarbonate, and sodium bicarbonate), bone (e.g., demineralized bone, bone morphogenetic protein, allograft bone and/or autologous bone), calcium phosphate, siliconized calcium phosphate, substituted calcium phosphates (e.g., with magnesium, strontium, or silicate), calcium pyrophosphate, hydroxyapatite, polymethylmethacrylate, glass-ionomer, absorbable phosphate glass, calcium sulfate, tricalcium phosphate (e.g., beta tricalcium phosphate), or any combination thereof.

In certain embodiments, the optional additive material is present in an amount of from about 0.01% to about 80% by weight of the composition. In certain embodiments, the additive material is present in an amount of 5% to 10%, 10% to 20%, 25% to 35%, 20% to 40%, 35% to 55%, 50% to 70%, 65% to 80% or more than 80% by weight of the composition.

In certain embodiments, the optional additive is present in nano-scale particle sizes, but may also be present in micron or millimeter particle sizes or mixtures thereof.

Other Optional Additives

The compositions disclosed herein may also optionally comprise one or more "cell openers." Non-limiting examples include ORTOGEL501 (Goldschmidt) and X-AIR (Specialty Polymers & Services). In certain embodiments, the cell openers are present in an amount in of from about 0.1% to 5% by weight of the composition. In one embodiment, the cell openers are present in an amount in of from about 1% to 2% or 1% to 3% by weight of the composition.

The compositions described herein may also optionally comprise one or more antibiotics. Non-limiting examples of suitable antibiotics include broad spectrum antibiotics (e.g., gentamicin, clindamycin, erythromycin), gram-positive and gram-negative families of antibiotics (e.g., ampicillins and cephalosporins).

The compositions of the invention may also optionally comprise one or more local anesthetics. Non-limiting examples include lidocaine, bupivacaine, tetracaine, and ropivacaine, including the freebases their salts and derivatives thereof.

The compositions may also optionally comprise one or more antioxidants. Non-limiting examples of suitable antioxidants include Vitamin E acetate, IRGANOX 1010 and IRGANOX 1035 (Ciba Geigy), and CYANOX 1790 and CYANOX 2777 (Cytec Industries). In certain embodiments, the antioxidant is present in an amount of from about 0.01% to 5% by weight of the composition.

In certain embodiments, a steroid-based compound, such as an intracellular messenger, may optionally be included in the compositions described herein to modulate the rate of bone growth. In some embodiments, progenitor cells optionally may be included in the compositions of the invention.

Clinical Applications

Component putties may be mixed to relative homogeneity by hand or with a mixing apparatus such as a mortar and pestle to produce the final product compositions as described herein. Depending upon the specific reaction being employed, the final product composition will begin to harden over time. During this phase, the compositions may be applied to the body for its intended use. In some embodiments, the compositions may be applied to bleeding bone to act as a hemostatic tamponade. In other embodiments, the compositions may be applied as an adhesive, e.g., to stabilize a bone fracture or reapproximate a sternotomy. In other embodiments, the compositions may be applied as a bone void filler to aid in the healing of bone defects, as a bone cement to fill gaps in the skeletal system, result in skeletal fusion or aid in the adhesion between bone segments, fragments and/or metallic hardware. The compositions described herein can be custom shaped by a clinician to create form fitting fixation devices such as sheets, rods, wraps or other support structures that may be anchored by plates, sutures or screws.

Hardened Polymer

A hardened polymer, preferably containing an osteoconductive filler, may be ground to a fine powder and used, as such, or converted into a putty by mixing with a suitable vehicle, to fill bone voids and other orthopedic defects. The component putty concept could be used during manufacturing as an alternative to "conventional" polymerization using liquids and fillers to form fully cured materials due to the improved handling properties that eliminate liquid and taffy phases of polymerization.

Water

In certain embodiments, the compositions of the invention contain no added water. In some embodiments, the compositions are anhydrous. In certain embodiments where there is no added water, water may nevertheless be present in small amounts. For example, certain commercially-available polyols comprise a mixture of the polyol and a small amount of water. In addition, certain optional particulate materials as described herein, such as calcium carbonate may comprise bound water. Formulating the compositions in an atmosphere that contains moisture may also result in the incorporation of water into the compositions. In certain embodiments of the present invention, the compositions are prepared under a nitrogen purge that comprises a desired amount of moisture, thereby controlling the water content of the compositions. In other embodiments, water may be added to the compositions during the process of their formation from the component parts. In other embodiments, the compositions are prepared under essentially water-free conditions with anhydrous components such that the resulting compositions are essentially anhydrous.

In certain embodiments, water is present in the compositions being made in an amount from at least about 0.01% to about 3% by weight of the composition. In certain embodiments, water is present in an amount of from about 0.05% to 1%, from about 0.05% to 1.5%, from about 0.1% to 1%, from about 0.1% to 1.5%, from about 0.1% to 2%, from about 1% to 2%, or from about 2% to 3%.

Particulate Materials

Both the putty- and non-putty compositions of the invention may contain optional particulate materials. In one embodiment, the particulate material is an osteoconductive material. In certain embodiments, the particulate material supports or promotes the growth of bone at the application site. In certain embodiments, the mean particle size of the optional particulate material is in the micron or submicron range. In one embodiment, the mean particle size is from about 0.001 to 0.100 microns, from about 0.100 to 5 microns, from about 5 to 100 microns, from about 5 to 500 microns, or from about 500 to 1000 microns.

In one embodiment, the optional particulate material is a carbonate or bicarbonate, e.g., calcium carbonate, magnesium carbonate, aluminum carbonate, iron carbonate, zinc carbonate, calcium bicarbonate, and sodium bicarbonate, or any combination thereof. In one embodiment, the optional particulate material is bone (e.g., demineralized bone, bone morphogenetic protein, allograft bone, and/or autogenous bone), calcium phosphate, siliconized calcium phosphate, substituted calcium phosphates (e.g., with magnesium, strontium, or silicate), calcium pyrophosphate, hydroxyapatite, polymethyl methacrylate, glass-ionomer, absorbable phosphate glass, calcium sulfate, tricalcium phosphate (e.g., beta tricalcium phosphate), or any combination thereof. Other examples include poly ether ether ketone (PEEK), REPLACE (Cortek, Inc.), EXPANCEL (Akzo Nobel). In other embodiments, the particulate material is a ceramic such as substituted calcium phosphates (e.g, silicate, strontium or magnesium substitution) or a glass such as bioglass. In some embodiments, the particulate material is one or more of calcium sulfate, calcium phosphosilicate, sodium phosphate, calcium aluminate, calcium phosphate, hydroxyapatite, demineralized bone, or mineralized bone. The optional particulate material, when present, may comprise any one or more of the materials listed in the embodiments above. In one embodiment, the particulate material, if present in the composition, does not comprise calcium carbonate.

In certain embodiments, the optional particulate material is present in an amount of from about 0.01% to about 10% by weight of the composition. In certain embodiments, the optional particulate material is present in an amount of 0.10% to 10%, 1% to 10%, or 5% to 10%. In other embodiments, the optional particulate material is present in an amount of from about 10% to about 20% by weight of the composition, or from about 20% to 30%, about 30% to 40%, about 40% to 50%, about 50% to 60%, about 60% to 70% or about 70% to 80% by weight of the composition.

Foaming Agents

In certain embodiments, an optional foaming agent may be included in the process of forming the compositions of the invention, for example to modulate pore size. Carboxylic acids may act as foaming agents by reacting with isocyanates to form carbon dioxide (and the corresponding amide). Non-limiting examples of carboxylic acids that can be used in this manner are benzoic acid, malic acid, and succinic acid. In certain embodiments, the compositions of the invention are formed by a process of combining a polyol and/or polyamine, a polyisocyanate, and a carboxylic acid. In one embodiment, the compositions formed with a carboxylic acid do not contain water. In another embodiment, the compositions formed with a carboxylic acid do not contain added water. In another embodiment, albumen is used as a foaming agent with or without sodium alginate to form the compositions of the invention. In another embodiment, hydrogen peroxide is used as a foaming agent to form the compositions of the invention.

Catalyst Component

In certain embodiments an optional catalyst is added, e.g., to the polyol that is combined with the isocyanate to form the compositions of the invention. In certain embodiments, at least one catalyst is present in an amount sufficient to ensure that the polymerization reactions have proceeded to completion before the compositions are placed within the body of a mammal. Non-limiting examples of catalysts include a tertiary amine (e.g., DABCO 33LV, Air Products, Inc.) and organometallic compounds such as, for example, stannous octoate, and dibutyl tin dilaurate (e.g., DABCO T12, Air Products, Inc.). In certain embodiments, the catalyst may remain in the composition after its formulation and curing, e.g., as a monomer that is present in the matrix of the solidified form of the composition. A non-limiting example of such a catalyst is N,N,N'-Tri(2-hydroxylpropyl)-N'-hydroxyethyl ethylene diamine (POLY-Q-40-800, Arch Chemicals, Inc.).

In certain embodiments, the catalyst is present in the polyol in an amount of from about 0.05% to about 0.5% by weight of the polyol. In certain embodiments, the catalyst is present in an amount of from about 0.15% to about 0.4% by weight of the polyol.

Optional Surfactant Component

In certain embodiments, an optional surfactant is included in the process of forming the compositions of the invention in order to control the porosity of the composition including the size and/or shape of pores within the composition. Non-limiting examples of suitable surfactants include DABCO DC 193 and DABCO DC 5241 (Air Products, Inc.), MAXEMUL 6106 and MAXEMUL 6112 (Uniqema), and silicone surfactants (e.g., those available from Struktol Corp.).

Radiotransparent/Radiopaque Component

In the multi-putty embodiment, in many instances the filler used will be radiopaque (eg calcium phosphate granules) and impart radioopacity to the hardened formulation. In certain other embodiments, an optional radiotransparent and/or a radiopaque substance is included in the compositions of the invention. Non-limiting examples of a radiotransparent substance include air, nitrogen gas, carbon dioxide, and oxygen gas. Non-limiting examples of a radiopaque substance include ceramic particles (eg calcium phosphate) barium sulphate ($BaSO_4$) and zirconium dioxide ($ZrO_2$). Examples of commercially available radiopaque substances include LIPIODOL, HYPAQUE, and OMNIPAQUE. The at least one radiotransparent substance and/or radiopaque substance, when present, is present in the compositions in an amount of from about 5% to about 30% by weight of the composition, and, in certain embodiments, from about 10% to about 20% by weight of the composition.

Protein Component

The compositions of the present invention may optionally comprise one or more bioactive proteins, peptides, or polypeptides. Preferably, the one or more bioactive proteins, peptides, or polypeptides is active in the stimulation of bone growth. Non-limiting examples of suitable proteins include collagen, OP1 (Stryker Homedica), INFUSE (Medtronic Corp.), or any recombinant bone morphogenic protein. Preferably, the one or more bioactive proteins, peptides, or polypeptides is non-reactive with the other components of the composition, allowing it to be included at any point during the formulating process. Thus, when present, the one or more peptides is not incorporated into the polymer backbone, but instead is either embedded in the polymer matrix, dispersed in the composition, or adherent to the surface of the composition.

The one or more bioactive proteins, peptides, or polypeptides may be incorporated within the compositions for example, by inclusion in the process of combining the isocyanate component and the polyol/polyamine component. In this way, the one or more bioactive proteins, peptides, or polypeptides is dispersed throughout the composition. Alternatively, the one or more bioactive proteins, peptides, or polypeptides may be added after all other components have been combined, preferably from about 10 minutes to about 45 minutes after combination of the other components. In this way, the one or more bioactive proteins, peptides, or polypeptides adheres to an outer surface of the composition.

Optional Light- or Photo-Initiators

The compositions of the present invention may comprise light- or photo-initiators. Non-limiting examples of suitable light- or photo-initiators include 24650-42-8 (Loctite Corp). In a preferred embodiment, the light- or photo-initiators are included in compositions made from unsaturated components, e.g., isocyanate prepolymers having one or more double bonds, polyols having double bonds, or adducts formed from reactions between isocyanates and acrylates.

A photo- or light-initiator may be incorporated into the compositions, for example, by combining with a liquid component (e.g., an isocyanate, a polyol or polyamine, a chain-extender or crosslinker).

In certain embodiments, the compositions comprising a photo- or light-initiator solidify at an accelerated rate, e.g., in the range of from about 1 to 5 minutes or 1 to 10 minutes after exposure to a suitable energy source (e.g., a suitable light source).

Other Optional Additives

The compositions of the invention may also optionally comprise one or more "cell openers." Non-limiting examples include ORTOGEL501 (Goldschmidt) and X-AIR (Specialty Polymers & Services). In certain embodiments, the cell openers are present in an amount in of from about 0.1% to 5% by weight of the composition. In one embodiment, the cell openers are present in an amount in of from about 1% to 2% or 1% to 3% by weight of the composition.

The compositions of the invention may also optionally comprise one or more antibiotics. Non-limiting examples of suitable antibiotics include broad spectrum antibiotics (e.g., gentamicin, clindamycin, erythromycin), gram-positive and gram-negative families of antibiotics (e.g., ampicillins and cephalosporins).

The compositions of the invention may also optionally comprise one or more local anesthetics or analgesics. Non-limiting examples include lidocaine, bupivacaine, tetracaine, and ropivacaine. Further examples include benzocaine and fentanyl (a potent non-opioid).

The compositions of the invention may also optionally comprise one or more anti-inflammatory substances such as the non-specific ibuprofen and aspirin, or the COX-2 specific inhibitors such as rofecoxib and celeboxib.

The compositions of the invention may also optionally comprise one or more antioxidants. Non-limiting examples of suitable antioxidants include IRGANOX 1010 and IRGANOX 1035 (Ciba Geigy), and CYANOX 1790 and CYANOX 2777 (Cytec Industries). In certain embodiments, the antioxidant is present in an amount of from about 0.01% to 0.5% by weight of the composition.

In certain embodiments, a composition of the invention further comprises a colorant. Non-limiting examples of suitable colorants include gentian violet, D&C Violet #2, and D&C Green #6.

In certain embodiments, a steroid-based compound, such as an intracellular messenger, may optionally be included in the compositions of the invention to modulate the rate of bone growth. In some embodiments, progenitor cells optionally may be included in the compositions of the invention.

EXAMPLES

The following example describes the preparation of a number of multiputty compositions using a resorbable polyurethane system. The putties were made by mixing either a liquid isocyanate or a polyol solution with particulate calcium salts. Enough calcium salt was added to establish suitable handling properties. For all isocyanate putties, [5-[2-[2-(4-Isocyanatobenzoyl)oxypropanoyloxy]-ethoxy]-1-methyl-2-oxo-pentyl]-4-isocyanatobenzoate, also referred to as "ALD", was the isocyanate used. All polyol based putties used a polyol solution that consisted of polycaprolactone diol (molecular weight=530 KDa) and 1,4-butane diol in a 40%:60% molar ratio, respectively.

In one experiment, three different filler types, HA-TCP, calcium carbonate, and anhydrous dibasic calcium phosphate (at amounts ranging between 50-70%) and concentration of isocyanate and polyol/extender mixtures were varied. The compositions also varied the filler particle size, i.e., nanometer, micrometer (small), and millimeter (medium).

For formulations comprising calcium carbonate, 50% of projected weight percent calcium carbonate (Component C) was weighed in a plastic cup. Isocyanate (Component A) was added to the cup and mixed with the calcium carbonate. Another 20% of calcium carbonate (70% of total sample weight) was added to the cup and mixed for 2-3 minutes to obtain a uniform composition. Caprolactone 530 and butanediol (Component B) was then added to the mixture and stirred for another minute. This mixture was then applied to a wet bone surface. It was spreadable for up to 1-2 minutes, after which it transformed into a cohesive hard putty that was no longer spreadable.

For formulations with HA-TCP, 70% of projected weight percent HA-TCP was weighed in a plastic cup. Isocyanate was added to the cup and mixed for a minute to obtain a uniform composition. Caprolactone 530 and butanediol was then added to the mixture and stirred for another minute. After 2-3 minutes, the mixture was applied to a wet bone surface. It was not spreadable and was more granular compared with calcium carbonate. After 5-6 minutes, it transformed into a cohesive putty. In general, calcium carbonate (up to 70%) performed better in spreadability and adhesion to bone compared with HA-TCP. Finer particle sizes appeared to work better.

In another experiment, the hydrophilicity and molecular weight of polyol/extender combinations (Component B) were varied, with the objective of extending putty composition pot life. Here, calcium carbonate was mixed with isocyanate, forming a composition having a putty-like consistency. Pluronic L-35 (much more hydrophilic than caprolactone 530) and butanediol was then added and mixed for another 2 minutes to obtain a uniform composition. After 3 minutes, it was viscous and sticky. It was then applied on a wet bone surface and was spreadable for up to 20 minutes. The reaction of Pluronic with isocyanate was slower than with Caprolactone 530. Additional experiments using less Pluronic were performed, with Caprolactone 530 as the polyol mixture. To improve rigidity, lower molecular weight PEGs were also used in subsequent experiments.

In another experiment, prepolymers/salts were used as a hemostat, followed by isocyanate/salt/polyol/extender mixtures as adhesive adherents to previously applied hemostats. Here, calcium carbonate (70% of total projected sample weight) was weighed in a plastic cup. Isocyanate was added to the cup and mixed for 2 minutes to obtain a uniform composition. This mixture was then applied to a wet bone. Spreadability and adhesion appeared to be good. Component B (Caprolactone 530 and butanediol without salt) at a 5% concentration was then added to the mixture and mixed for another minute to form a prepolymer. After 3 minutes, the mixture turned into a coherent putty that was hard and non-spreadable. It was found that component A (isocyanate) in combination with a filler (calcium carbonate) can be used as a bone hemostat. Further experiments were conducted to determine the efficacy of the prepolymer concept by varying the isocyanate/polyol ratio or combining a Pluronic with Caprolactone 330 to reduce the rate of reaction.

General Putty Observations

Table 1 provides a summary of the putty compositions disclosed herein. All ALD putties displayed excellent hand feel, holding their shape upon storage and did not stick to gloves. All putties formed possessed a smooth texture with little evidence of calcium salt granules, regardless of composition or size. Polyol putties displayed varying amounts of creep upon storage depending on composition. Options for reducing creep included increasing the particulate calcium salt content. Alternatively, viscosity of the liquid component was adjusted through the use of a viscosity-increasing partial reaction of the liquid components. This strategy is exemplified in example #12 where a partially pre-reacted putty was used.

TABLE 1

Exemplary putty compositions

| # | Putty | Liquid reactive components (wt %) | Additive Filler (wt %) | Component Putty Observations | Putty C Observations |
|---|---|---|---|---|---|
| 1 | A | ALD (27%) | $CaCO_3$ (73%) | | Workable for about 10 min.; appeared fully hardened after 24 hrs; final putty was hard and stiff. |
|   | B | Polyol (21%) | $CaCO_3$ (79%) | Excellent handling properties | |
| 2 | A | ALD (67%) | HA (nanocrystals) (33%) | Putty hardened after storage overnight in a sealed contained, likely due to reaction between HA and ALD | Workable for about 10 min.; appeared fully hardened after 24 hrs with slightly sticky feel during hardening. |
|   | B | Polyol (57%) | HA (nanocrystals) (43%) | Poor handling properties (crumbly) | |
| 3 | A | ALD (39%) | DCP (61%) | | Workable for about 10 min.; appeared fully hardened after 24 hrs; final putty was hard and stiff. |
|   | B | Polyol (35%) | DCP (65%) | Poor handling properties (crumbly) | |
| 4 | A | ALD (48%) | β-TCP (5 μm) (52%) | | Workable for about 10 min.; appeared fully hardened after 24 hrs; final putty was hard and stiff. |
|   | B | Polyol (43%) | β-TCP (5 μm) (57%) | Good handling properties | |
| 5 | A | ALD (49%) | β-TCP (nanocrystals) (51%) | | Workable for about 10 min.; appeared fully hardened after 24 hrs; final putty was hard and stiff. |
|   | B | Polyol (43%) | β-TCP (nanocrystals) (57%) | Good handling properties | |
| 6 | A | ALD (27%) | HA/TCP (250-630 μm) (51%) + β-TCP (5 μm) (22%) | | Workable for about 10 min.; appeared fully hardened after 24 hrs; final putty was hard and stiff. |
|   | B | Polyol (24%) | HA/TCP (250-630 μm) (49%) + β-TCP (5 μm) (27%) | Good handling properties | |
| 7 | A | ALD (37%) | TCP (100-300 μm) (43%) + β-TCP (5 μm) (20%) | | Workable for about 10 min.; appeared fully hardened after 24 hrs; final putty was hard and stiff. |
|   | B | Polyol (43%) | TCP (100-300 μm) (35%) + β-TCP (5 μm) (22%) | Good handling properties | |
| 8 | A | ALD | HA/TCP (250-630 μm) + DCP | Good handling properties | Workable for about 10 min.; appeared fully hardened after 24 hrs; final putty was hard and stiff. |
|   | B | Polyol | HA/TCP (250-630 μm) + DCP | Good handling properties | |
| 9 | A | ALD | HA/TCP (250-630 μm) + $CaCO_3$ | Good handling properties | Workable for about 10 min.; appeared fully hardened after 24 hrs; final putty was hard and stiff. |
|   | B | Polyol | HA/TCP (250-630 μm) + $CaCO_3$ | Good handling properties | |

TABLE 1-continued

Exemplary putty compositions

| # | Putty | Liquid reactive components (wt %) | Additive Filler (wt %) | Component Putty Observations | Putty C Observations |
|---|-------|-----------------------------------|------------------------|------------------------------|----------------------|
| 10 | A | ALD (27%) | HA/TCP (250-630 μm) (51%) + β-TCP (5 μm) (22%) | | Workable for about 10 min.; appeared fully hardened after 24 hrs; final putty was hard and stiff. |
|    | B | Polyol (28%) | HA/TCP (250-630 μm) (55%) + HA (17%) | Poor handling properties (crumbly) | |
| 11 | — | ALD (26%) | HA/TCP (250-630 μm) (51%) + β-TCP (5 μm) (13%) | Good handling properties; does not stick to gloves; putty holds shape; large granules were not apparent by feel through gloves | Not combined to form polyurethane. |
| 12 | A | ALD (27%) | HA/TCP (250-630 μm) (51%) + β-TCP (5 μm) (22%) | | Workable for about 10 min.; appeared fully hardened after 24 hrs; final putty was hard and stiff. No apparent difference than using straight ALD and polyol putties to form polyurethane. |
|    | B | ALD (27%)% + polyol (36%) | β-TCP (5 μm) (37%) | Good handling properties, similar feel to ALD putties; does not stick to gloves; putty holds shape like ALD putties | |

TCP = Tricalcium phosphate
CaCO$_3$ = calcium carbonate
β-TCP = beta tricalcium phosphate
HA = hydroxyapatite
DCP = Dicalcium phosphate anhydrous
HA/TCP = Hydroxyapatite/beta tricalcium phosphate Mixed Putty Observations Polyurethane/calcium salt composites were formed by combining isocyanate and polyol putties (or in one case an isocyanate and prepolymer putty) in an approximately 1:1 molar ratio of isocyanate to polyol. Composites were formed using putties with the same calcium salt compositions or different compositions. After mixing two reactive putties, the combined putty is exothermic, softens slightly and becomes slightly sticky, before hardening over time. All individual putties are spreadable and workable over cut bone surfaces. Combined putties are spreadable over cut bone surfaces or workable for a period of time prior to hardening. No major differences were apparent in the working time for all composites formed.

Clinical Example A: Sternotomy Hemostasis Device and Cement

An absorbable dual putty settable polyurethane system was prepared by mixing the following components that were stored separately in moisture-free containers:

Putty A:

| Absorbable diisocyanate (ALD) | 27.0% |
|---|---|
| Calcium carbonate | 71.6 |
| Caprolactone 530/16 parts | 1.4 |

Putty B:

| Caprolactone 530 | 16.0% |
|---|---|
| Butanediol | 5.0 |
| Calcium carbonate | 77.6 |
| ALD | 1.4 |

In preparation for a coronary artery bypass procedure, the thoracic cavity was opened using a midline incision of the sternum. Putty B was manually applied to both edges of the sawed sternum to control bleeding. Putty B, which is not a reactive hemostat, stops bleeding by blockading cut bone channels, through which blood escapes, causing static blood behind the putty to spontaneously clot (tamponade).

Following the surgical procedure which lasted several hours, the edges of the cut sternum are cleaned with gauze sponges and examined for any areas of re-bleeding to which, if found, additional Putty B was applied to ensure complete hemostasis.

A bead of Putty A was deposited along the entire length of one edge of the cut sternum which was then approximated to the other edge and pressed together. Stainless steel wire was placed to firmly hold the sternum edges together while the polyurethane cured overnight and thereby helps prevent painful stress-related shear motion. Healing bone growth occurred as the polyurethane was absorbed.

Clinical Example B: Sternotomy Hemostasis Device and Cement

The same dual putty system prepared for Clinical Example A is used in Clinical Example B. In this example, Putty A and Putty B were mixed by kneading and applied to the split sternum as a hemostatic agent. After hemostasis was achieved, the surgery was carried out and, at the conclusion, a fresh bead of the two-putty mixture was applied to one edge of the sternum before the two edges were reapproximated and reinforced with wire or other hardware. Adhesion to the previously placed hemostatic polyurethane was satisfactory.

EQUIVALENTS

Those skilled in the art will recognize or be able to ascertain using no more than routine experimentation, many equivalents to the specific embodiments of the invention described herein. Such equivalents are intended to be encompassed by the following claims.

All references cited herein are incorporated herein by reference in their entirety and for all purposes to the same extent as if each individual publication or patent or patent application was specifically and individually indicated to be incorporated by reference in its entirety for all purposes.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. A sterile, body-absorbable composition comprising at least two separate reactive putties which can be hand mixed or kneaded together to form a settable polyurethane or polyureaurethane putty composition which hardens into its fully cured solid form at room temperature and body temperature,
    the first putty comprising a prepolymer and one or more diisocyanates in amounts sufficient to produce a putty,
    the at least second putty comprising a prepolymer and one or more polyols, polyamines, or polyols and polyamines in amounts sufficient to produce a putty,
    wherein each putty independently optionally further comprises a particulate component such that the amount of the particulate material in the settable composition is in a range of from about 50%-60%, 60%-70%, or 70%-80% of the composition by weight, and
    wherein the settable composition optionally comprises between 5% to 10% of one or more additive materials.

2. The composition of claim 1, wherein the one or more diisocyanates is an aromatic isocyanate, an aliphatic isocyanate, a cycloaliphatic isocyanate, or an adduct of an isocyanate.

3. The composition of claim 2, wherein the one or more diisocyanates is an aromatic di- or polyisocyanate-having at least one hydrolysable linkage bridging at least two of the aromatic rings.

4. The composition of claim 3, wherein the hydrolysable linkage is derived from glycolic acid, lactic acid, or a polycaprolactone.

5. The composition of claim 1, wherein the one or more polyols is selected from the group consisting of butanediol, polytetramethylene ether glycol, tris-hydroxymethyl propane, monosubstituted tris-hydroxymethyl propane, pentaerythritol, monosubstituted pentaerythritol, hydrogenated dihydroxypolyisoprene, hydroxyl terminated polybutadiene, hydroxyl terminated homopolymers or copolymers of glycolide, lactide, p-dioxanone, trimethylene carbonate and/or caprolactone, polyethylene glycol, and a random or block copolymer of ethyelene oxide and propylene oxide.

6. The composition of claim 5, wherein the one or more polyols is hydrolysable.

7. The composition of claim 1, wherein the one or more polyamine is selected from a primary polyamine, a secondary polyamine, or a hindered polyamine.

8. The composition of claim 7, wherein the one or more polyamines is selected from ethylene diamine, 1,2-propane diamine, 1,3-propane diamine, butane diamine, cyclopentane diamine, cyclohexane diamine and hexamethylene diamine.

9. The composition of claim 1, further comprising a crosslinker.

10. The composition of claim 2, further comprising a chain extender.

11. The composition of claim 1, wherein the particulate material has a mean particle size from about 5 to 500 microns.

12. The composition of claim 11, wherein the particulate material is selected from the group consisting of calcium phosphate; siliconized calcium phosphate; calcium phosphate substituted or augmented with magnesium, strontium, or silicate; calcium pyrophosphate; hydroxyapatite; polymethyl methacrylate; glass-ionomer; absorbable phosphate glass; calcium sulfate; tricalcium phosphate; bone; demineralized bone; mineralized bone; glass; bioglass; and any combination thereof.

13. The composition of claim 11, wherein the particulate material comprises particles of bone in the form of demineralized bone, allograft bone, autogenous bone, or combinations thereof.

14. The composition of claim 1, wherein the additive material is selected from the group consisting of carbonate or bicarbonate selected from calcium carbonate, sodium carbonate, magnesium carbonate, aluminum carbonate, iron carbonate, zinc carbonate, calcium bicarbonate, sodium bicarbonate, a bicarbonate of magnesium, aluminum, iron, or zinc; embedded particles of bone; demineralized bone; bone morphogenetic protein; vitamin E acetate; a fatty alcohol ester; a divalent salt of a fatty acid; triethanolamine; and combinations thereof.

15. The composition of claim 1, wherein at least one of the putties comprises one or more additive components selected from the group consisting of starch, carboxymethyl starch, carboxymethyl cellulose, oxidized cellulose, antimicrobials, surfactants, proteins, colorants, radiopaque agents and water, and mixtures thereof.

16. The composition of claim 1, wherein at least one of the putties comprises one or more additive components selected from the group consisting of a tertiary amine, stannous octoate and dibutyl tin dilaurate, and combinations thereof, as a catalyst for accelerating the rate of cure.

17. The composition of claim 1, further comprising one or more additives selected from an antioxidant, an antibiotic, an antimicrobial, an anesthetic, an analgesic, a plasticizer, or an anti-inflammatory agent.

18. The composition of claim 1, wherein the settable composition is fully or partially biodegradable, absorbable under physiological conditions, or both fully or partially biodegradable and bioabsorbable under physiological conditions.

* * * * *